(12) United States Patent
Yun et al.

(10) Patent No.: US 12,030,859 B2
(45) Date of Patent: Jul. 9, 2024

(54) POLYMERIZABLE COMPOUND, POLYMERIZABLE COMPOSITION AND OPTICAL FILM

(71) Applicant: DONGJIN SEMICHEM Co., Ltd., Incheon (KR)

(72) Inventors: Ji Ho Yun, Hwaseong-si (KR); Young Kuk Kim, Hwaseong-si (KR); Sung Il Yoon, Hwaseong-si (KR); Jun Yong Song, Hwaseong-si (KR); Seung Hyup Shin, Hwaseong-si (KR); Jin Wuk Kim, Hwaseong-si (KR)

(73) Assignee: DONGJIN SEMICHEM CO., LTD., Incheon (KR)

( * ) Notice: Subject to any disclaimer, the term of this patent is extended or adjusted under 35 U.S.C. 154(b) by 451 days.

(21) Appl. No.: 17/111,931

(22) Filed: Dec. 4, 2020

(65) Prior Publication Data
US 2021/0171478 A1    Jun. 10, 2021

(30) Foreign Application Priority Data

Dec. 4, 2019 (KR) .................. 10-2019-0160046

(51) Int. Cl.
*C07D 277/66* (2006.01)
*C07D 333/58* (2006.01)
*C08F 261/04* (2006.01)
*G02B 1/04* (2006.01)
*G02B 5/30* (2006.01)

(52) U.S. Cl.
CPC ......... *C07D 277/66* (2013.01); *C07D 333/58* (2013.01); *C08F 261/04* (2013.01); *G02B 1/04* (2013.01); *G02B 5/3083* (2013.01)

(58) Field of Classification Search
CPC .......................... C07D 277/66; C07D 333/58
See application file for complete search history.

(56) References Cited

U.S. PATENT DOCUMENTS

2018/0327668 A1* 11/2018 Horiguchi .............. C09K 19/54

OTHER PUBLICATIONS

Okawa et al. 2009 (CN 101470212) . Abstract.*

* cited by examiner

*Primary Examiner* — Bruck Kifle
(74) *Attorney, Agent, or Firm* — LEX IP MEISTER, PLLC

(57) ABSTRACT

Proposed are a polymerizable compound, a polymerizable composition, and an optical film using the same, which can exhibit superior optical properties in a wide wavelength range by reducing wavelength dependence or exhibiting reverse-wavelength dispersibility.

3 Claims, 3 Drawing Sheets

POLYMERIZABLE COMPOUND, POLYMERIZABLE COMPOSITION AND OPTICAL FILM

CROSS REFERENCE TO RELATED APPLICATION

The present application claims priority to and the benefit of, under 35 U.S.C. § 119, Korean Patent Application No. 10-2019-0160046, filed on Dec. 4, 2019, the entire content of which is incorporated herein for all purposes by this reference.

BACKGROUND OF THE DISCLOSURE

1. Technical Field

The present disclosure relates to a polymerizable compound, a polymerizable composition, and an optical film.

2. Description of the Related Art

A flat panel display (FPD) is configured to include a member using an optical film such as a polarizing plate or a retardation plate. Here, the optical film may be obtained by dissolving a polymerizable compound in a solvent to afford a solution, applying the solution on a supporting substrate, and then performing polymerization.

Meanwhile, it is known that the retardation (Re($\lambda$)) of an optical film caused by radiation of light having a wavelength of $\lambda$ nm is determined by the product of the birefringence index (an) and the film thickness (d) (Re($\lambda$)=$\Delta n \times d$). In addition, wavelength dispersibility is usually a value (Re($\lambda$)/Re(550)) obtained by dividing the retardation value (Re($\lambda$)) at an arbitrary wavelength of $\lambda$ nm by the retardation value (Re(550)) at 550 nm. The case in which the wavelength dispersibility (Re($\lambda$)/Re(550)) is close to 1, or the wavelength dispersibility at 450 nm [Re(450)/Re(550)]<1 and the wavelength dispersibility at 650 nm [Re(650)/Re(550)]>1 is referred to as reverse-wavelength dispersibility. It is known that constant polarization conversion is possible in a wavelength range showing reverse-wavelength dispersibility.

SID Symposium Digest of Technical Papers, 2006, Vol. 37, p. 1673 discloses, as a polymerizable compound, a compound (LC242) represented by the following chemical formula.

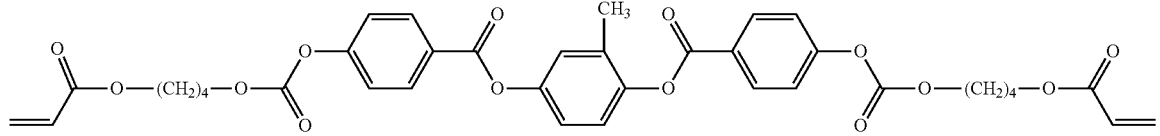

SUMMARY OF THE DISCLOSURE

Accordingly, some example embodiments of the present disclosure provide a polymerizable compound, a polymerizable composition, and an optical film using the same, which may exhibit superior optical properties in a wide wavelength range by reducing wavelength dependence or exhibiting reverse-wavelength dispersibility.

Some example embodiments of the present disclosure is to provide a polymerizable composition including a polymerizable compound that exhibits an excellent liquid crystal phase at a relatively low temperature and has good solubility in an organic solvent.

According to some example embodiments of the present disclosure, a polymerizable compound containing a group represented by Chemical Formula (1-1) or Chemical Formula (1-2) below and a polymerizable group is provided:

Chemical Formula (1-1)

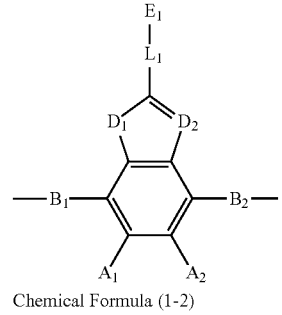

(1-1)

Chemical Formula (1-2)

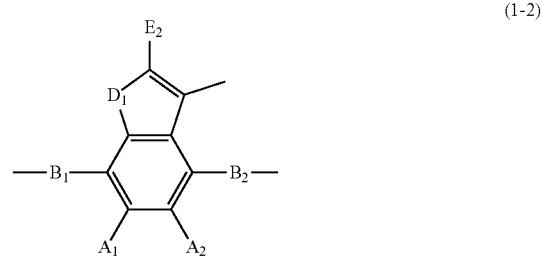

(1-2)

wherein, in Chemical Formula (1-1) and Chemical Formula (1-2), $A_1$ and $A_2$ each independently represent hydrogen, deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, a C2-C20 heterocycloalkyl group, a C6-C50 aryl group, or a C2-C50 heteroaryl group, each $D_1$ independently represents —$CR_1R_2$—, —S—, —$NR_2$—, —CO— or —O—, in which $R_1$ and $R_2$ each independently represent hydrogen or a C1-C6 alkyl group, each $D_2$ independently represents =$CR_3$— or =N—, in which $R_3$ independently represents hydrogen or a C1-C6 alkyl group, $E_1$ and $E_2$ each independently represent a substituted or unsubstituted C6-C60 aryl group, a substituted or unsubstituted C2-C60 heteroaryl group, or combinations thereof, in which, when $D_1$ is —S— and $D_2$ is =N— in Chemical Formula (1-1), $E_1$ contains an isothiocyanate group or a thiocyanate group as a substituent, $L_1$ is a direct bond or a C2-C10 alkynylene group having a triple bond, and $B_1$ and $B_2$ each independently represent a single bond or a divalent linking group.

According to some example embodiments of the present disclosure, a polymerizable composition including the polymerizable compound is provided.

According to some example embodiments of the present disclosure, an optical film that includes a polymer of the polymerizable compound and has reverse-wavelength dispersibility is provided.

According to some embodiments of the present disclosure, a polymerizable compound, a polymerizable composition, and an optical film using the same can exhibit superior optical properties in a wide wavelength range by reducing wavelength dependence or exhibiting reverse-wavelength dispersibility.

Moreover, an excellent liquid crystal phase at a relatively low temperature and good solubility in an organic solvent can be manifested.

The above effects and additional effects are described in detail below.

DESCRIPTION OF SPECIFIC EMBODIMENTS

Figure 1:
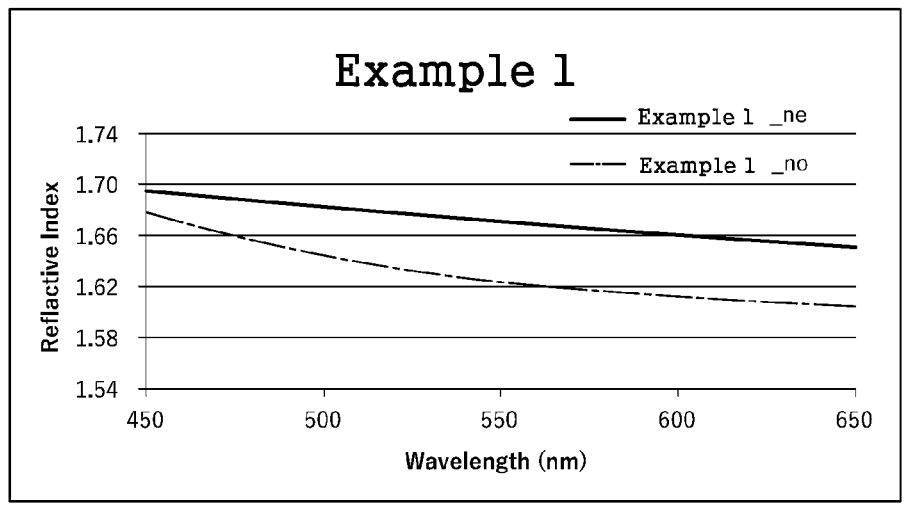
FIGS. 1 to 5 are graphs showing the refractive index depending on the wavelength of an optical film according to an embodiment of the present disclosure.

In the following description of the present disclosure, the terms used herein are merely intended to describe specific embodiments, and are not to be construed as limiting the scope of the present disclosure, which is defined by the appended claims. Unless otherwise defined, all technical or scientific terms used herein have the same meanings as those typically understood by persons having ordinary knowledge in the art to which the present disclosure belongs.

Unless otherwise stated, the terms "comprise", "comprises" and "comprising" are used to designate the presence of an object, a step, or groups of objects and steps described in the specification and claims, and should be understood as not excluding the presence or additional possibility of inclusion of any other objects, steps or groups of objects or steps.

When the term "about" is used in this specification in connection with a numerical value, it is intended that the associated numerical value include a tolerance of ±10% around the stated numerical value. When ranges are specified, the range includes all values therebetween such as increments of 0.1%.

As used herein, "at least one of A, B, or C," "one of A, B, C, or a combination thereof" and "one of A, B, C, and a combination thereof" refer to each constituent element, and a combination thereof (e.g., A; B; C; A and B; A and C; B and C; or A, B, and C).

Throughout the present specification and claims, the term "aryl" means those including a C6-050 aromatic hydrocarbon ring group, for example, an aromatic ring, such as phenyl, benzyl, naphthyl, biphenyl, terphenyl, fluorene, phenanthrenyl, triphenylenyl, perylenyl, chrysenyl, fluoranthenyl, benzofluorenyl, benzotriphenylenyl, benzochrysenyl, anthracenyl, stilbenyl, pyrenyl, etc.

Also, the term "heteroaryl" means those including a C2-C50 aromatic ring group containing at least one hetero element, for example, a heterocyclic group, such as pyrrolyl, pyrazinyl, pyridinyl, indolyl, isoindolyl, furyl, benzofuranyl, isobenzofuranyl, dibenzofuranyl, benzothiophenyl, dibenzothiophenyl, quinolyl, isoquinolyl, quinoxalinyl, carbazolyl, phenanthridinyl, acridinyl, phenanthrolinyl, thienyl, pyridine, pyrazine, pyrimidine, pyridazine, triazine, indole, quinoline, acridine, pyrrolidine, dioxane, piperidine, morpholine, piperazine, carbazole, furan, thiophene, oxazole, oxadiazole, benzoxazole, thiazole, thiadiazole, benzothiazole, triazole, imidazole, benzimidazole, pyran, dibenzofuran, etc.

Also, unless otherwise specifically defined, $L_x$ (in which x is an integer) in chemical formulas may represent a direct bond, a substituted or unsubstituted C6-C50 arylene group, or a substituted or unsubstituted C2-C50 heteroarylene group, and unless otherwise specifically defined, $R_x$ (in which x is an integer) may represent hydrogen, deuterium, a halogen, a nitro group, a nitrile group, a substituted or unsubstituted C1-C30 alkyl group, a substituted or unsubstituted C2-C30 alkenyl group, a substituted or unsubstituted C1-C30 alkoxy group, a substituted or unsubstituted C1-C30 sulfide group, a substituted or unsubstituted C6-C50 aryl group, or a substituted or unsubstituted C2-C50 heteroaryl group.

Throughout the present specification and claims, the term "substituted or unsubstituted" may mean substitution or non-substitution with at least one of deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C30 silyl group, a C3-C20 cycloalkyl group, a C2-C20 heterocycloalkyl group, a C6-C50 aryl group, and a C2-C50 heteroaryl group. Moreover, throughout the present specification, the same symbols have the same meanings unless otherwise specifically mentioned.

Also, —NCS represented in the structural formula means —NCS or —SCN.

Meanwhile, various embodiments of the present disclosure may be combined with other embodiments unless otherwise indicated. Hereinafter, embodiments of the present disclosure and effects thereof are described.

An embodiment of the present disclosure pertains to a polymerizable compound containing a group represented by Chemical Formula (1-1) or Chemical Formula (1-2) below and a polymerizable group.

Chemical Formula (1-1)

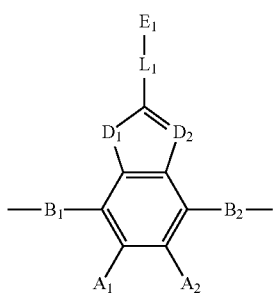

Chemical Formula (1-2)

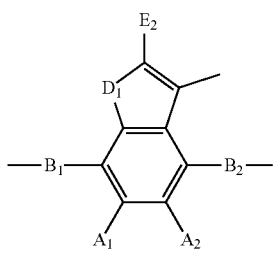

In Chemical Formula (1-1) and Chemical Formula (1-2),
$A_1$ and $A_2$ each independently represent hydrogen, deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, a C2-C20 heterocycloalkyl group, a C6-C50 aryl group, or a C2-C50 heteroaryl group, each $D_1$ independently represents —$CR_1R_2$—, —S—, —$NR_2$—, —CO— or —O—, in which $R_1$ and $R_2$ each independently represent hydrogen or a C1-C6 alkyl group, each $D_2$ independently represents =$CR_3$— or =N—, in which $R_3$ independently represents hydrogen or a C1-C6 alkyl group, $E_1$ and $E_2$ are each independently a substituted or unsubstituted C6-C60 aryl group, a substituted or unsubstituted C2-C60 heteroaryl group or combinations thereof, $L_1$ is a direct bond or a C2 to C10 alkynylene group having a triple bond, and $B_1$ and $B_2$ each independently represent a single bond or a divalent linking group. The divalent linking group is not limited, and examples thereof may include a substituted or unsubstituted C1-C30 alkyl group, a substituted or unsubstituted C3-C20 cycloalkyl group, a substituted or unsubstituted C2-C20 heterocycloalkyl group, a substituted or unsubstituted C6-C50 aryl group, a substituted or unsubstituted C2-C50 heteroaryl group, and combinations thereof, in which —$CH_2$— may be substituted with —C(=O)—, —C(=O)O—, —OC(=O)—, —O—, —S—, —C(=S)—, —C(=S)—O—, —O—C(=S)— or —NR—, and R may be hydrogen or a C1-C30 alkyl group.

When $D_1$ is —S— and $D_2$ is =N— in Chemical Formula (1-1), $E_1$ may contain, as a substituent, an isothiocyanate group or a thiocyanate group.

When $E_1$ contains an isothiocyanate group or a thiocyanate group, there are advantages in that the refractive index is increased, superior reverse-wavelength dispersibility is exhibited, and the phase transition temperature is decreased. Meanwhile, although not limited, the isothiocyanate group or thiocyanate group may also be present in $E_2$.

The polymerizable group is not limited, and may be connected to both ends of the polymerizable compound, namely to $B_1$ and $B_2$ of Chemical Formula (1-1) and Chemical Formula (1-2), and the number of polymerizable groups may be 2 to 4. When there are only two polymerizable groups at both ends, orientation may become apparent after polymerization. However, if the number of polymerizable groups exceeds 4, orientation may be lost because the groups may become entangled upon polymerization. The type of polymerizable group is not limited, so long as it is a group involved in the polymerization reaction, and specific examples thereof may include a vinyl group, a p-stilbene group, an acryloyl group, a methacryloyl group, an acryloyloxy group, a methacryloyloxy group, a carboxyl group, an acetyl group, a hydroxyl group, a carbamoyl group, a C1-C4 N-alkylamino group, an amino group, an epoxy group, an oxetanyl group, a formyl group, —N=C=O, —N=C=S, and the like.

The polymerizable compound according to an embodiment of the present disclosure may have a liquid crystal phase, particularly a nematic phase. Also, the polymerizable compound according to an embodiment of the present disclosure has a phase transition temperature in the range of about 0° C. to about 130° C., and is advantageous because the phase transition temperature is low. Specifically, the polymerizable compound according to an embodiment of the present disclosure may exhibit a liquid crystal phase in the range of about 20° C. to about 130° C., particularly in the range of about 70° C. to about 120° C. The low phase transition temperature of the polymerizable compound means that, during a series of processes of application of the composition including the polymerizable compound, UV irradiation, polymerization, and film formation, the processing temperature may be lowered. Accordingly, it is possible to more easily obtain an optically anisotropic film under mild conditions, and various problems caused by application of high temperatures may be prevented from occurring.

Meanwhile, each of $E_1$ and $E_2$ of Chemical Formula (1-1) or Chemical Formula (1-2) may be represented by any one selected from among Chemical Formulas Y-1 to Y-13 below.

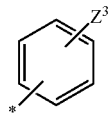

Y-1

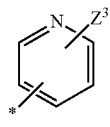

Y-2

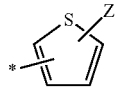

Y-3

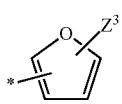 Y-4

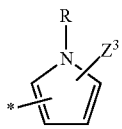 Y-5

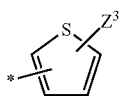 Y-6

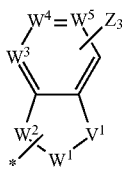 Y-7

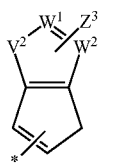 Y-8

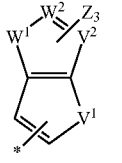 Y-9

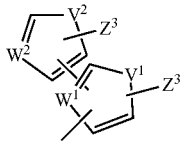 Y-10

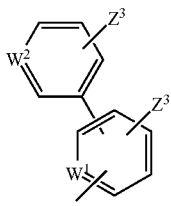 Y-11

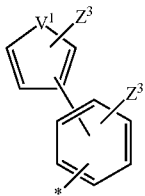 Y-12

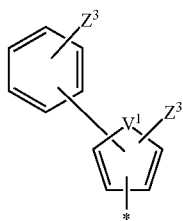 Y-13

In these chemical formulas, each $Z^3$ and R independently represents deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N alkylsulfamoyl group, a C2-C12 N,N-dialkylsulfamoyl group, a C3-C20 cycloalkyl group, a C2-C20 heterocycloalkyl group, a C6-C50 aryl group, or a C2-C50 heteroaryl group, $V^1$ and $V^2$ each independently represent —CO—, —S—, —$NR_3$—, —O—, —Se— or —$SO_2$—, in which $R_3$ independently represents hydrogen or a C1-C4 alkyl group, $W^1$ to $W^5$ each independently represent —$CR_4$= or —N=, in which $R_4$ independently represents hydrogen or a C1-C4 alkyl group, wherein at least one of $V^1$, $V^2$, and $W^1$ to $W^5$ contains S, N, O or Se, and is a linking portion with Chemical Formula (1-1) or Chemical Formula (1-2).

When $D_1$ is —S— and $D_2$ is =N— in Chemical Formula (1-1), $Z^3$ of Chemical Formula Y-1 may contain an isothiocyanate group or a thiocyanate group. In other cases, an isothiocyanate group or thiocyanate group may also be present.

Also, Chemical Formula (1-1) may be represented by Chemical Formula (1-3) below.

Chemical Formula (1-3)

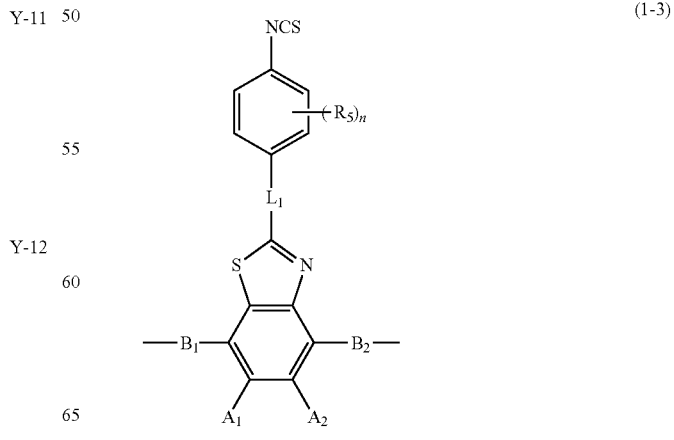

(1-3)

In Chemical Formula (1-3), L1, A1, A2, B1 and B2 are as defined in Chemical Formula (1-1), each $R_5$ is independently selected from among deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, a C2-C20 heterocycloalkyl group, a C6-C50 aryl group, and a C2-C50 heteroaryl group, and n is an integer of 0 to 4.

Also, Chemical Formula (1-2) may be represented by any one of Chemical Formula (1-4) and Chemical Formula (1-5) below.

Chemical Formula (1-4)

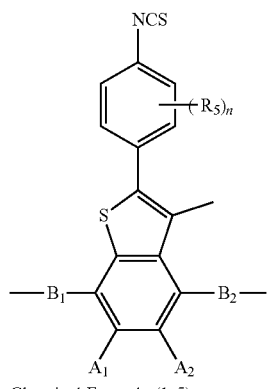

(1-4)

Chemical Formula (1-5)

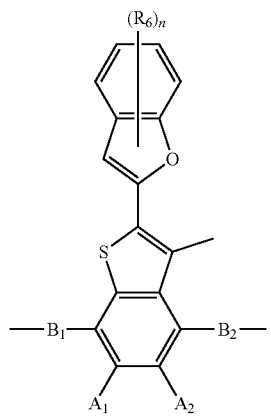

(1-5)

Here, $A_1$, $A_2$, $B_1$ and $B_2$ are as defined in Chemical Formula (1-2), $R_5$ and $R_6$ are each independently selected from among deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, a C2-C20 heterocycloalkyl group, a C6-C50 aryl group, and a C2-C50 heteroaryl group, and n is' independently an integer of 0 to 5 (in which n of Chemical Formula (1-4) is an integer of 0 to 4).

Specifically, Chemical Formula (1-1) may have a structure represented by any one selected from among the following chemical formulas. $B_1$ and $B_2$ are connected to both ends of the following structure.

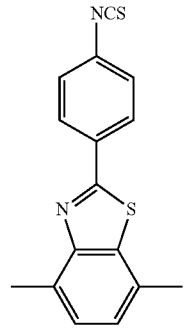

(1-1-1)

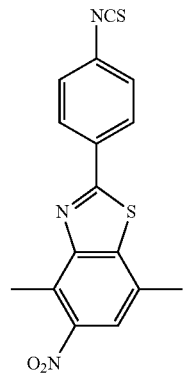

(1-1-2)

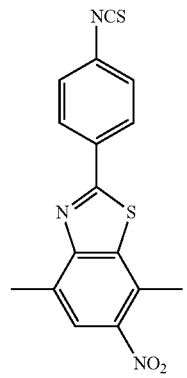

(1-1-3)

-continued
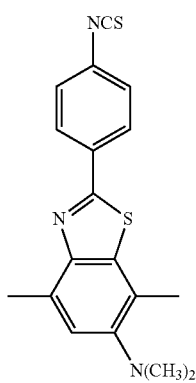
(1-1-4)
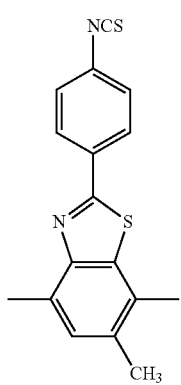
(1-1-5)
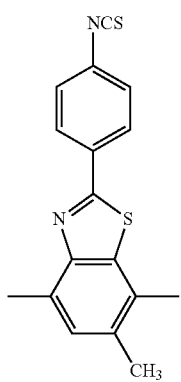
(1-1-6)
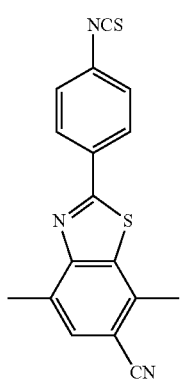
(1-1-7)
-continued
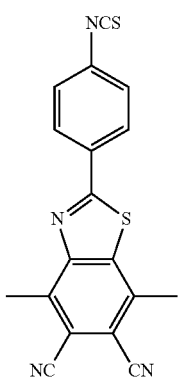
(1-1-8)
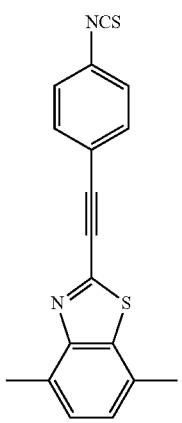
(1-1-9)
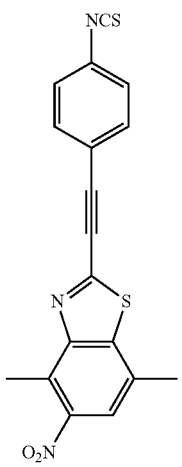
(1-1-10)

(1-1-11)
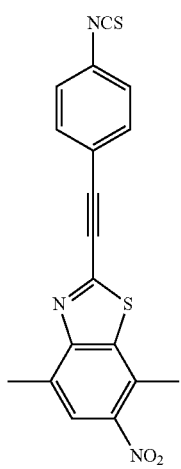
(1-1-12)
(1-1-13)
(1-1-14)
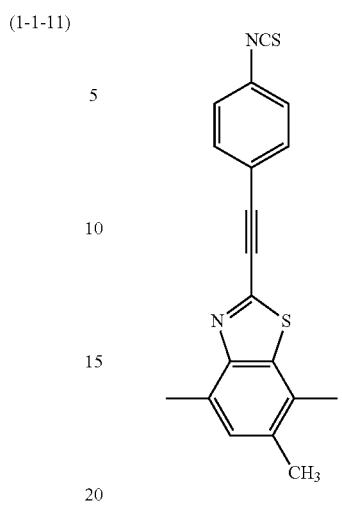
(1-1-15)
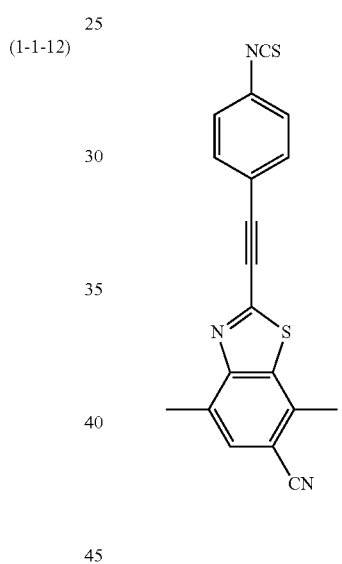
(1-1-16)
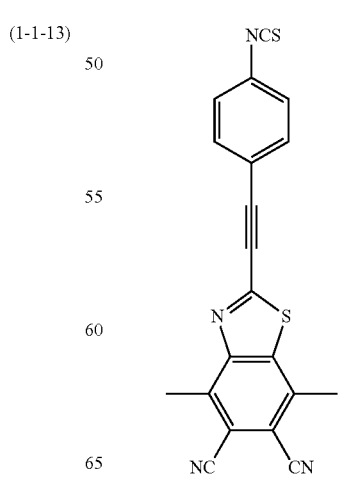

In addition, Chemical Formula (1-2) may have a structure represented by any one selected from among the following chemical formulas.

-continued
(1-2-9)
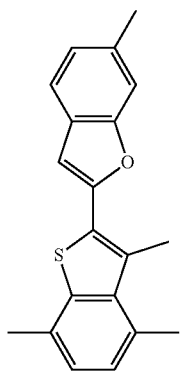
(1-2-10)
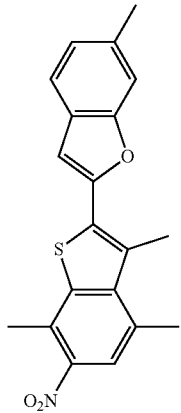
(1-2-11)
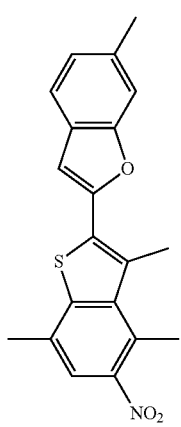
(1-2-12)
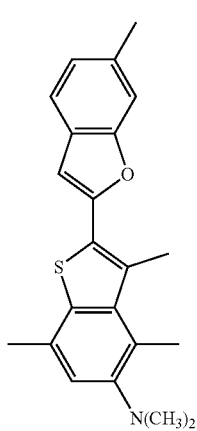
-continued
(1-2-13)
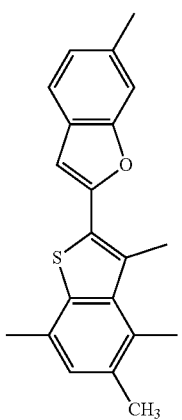
(1-2-14)
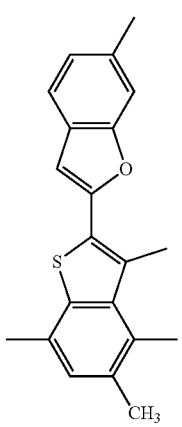
(1-2-15)
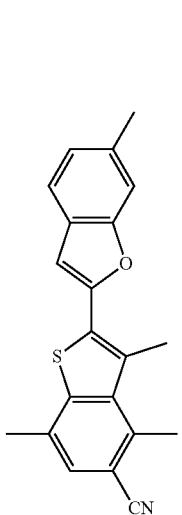

-continued

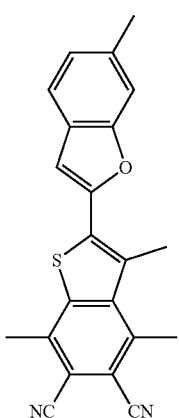

(1-2-16)

Also, Chemical Formula (1-1) or Chemical Formula (1-2) may be represented by Chemical Formula (1-6) or Chemical Formula (1-7) below.

Chemical Formula (1-6)

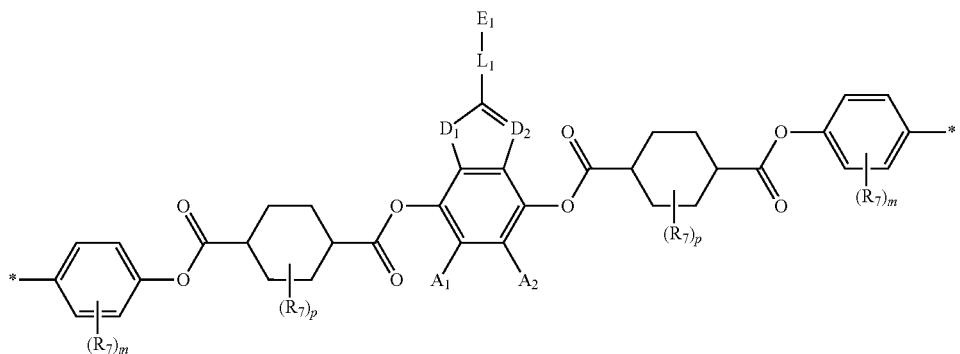

(1-6)

Chemical Formula (1-7)

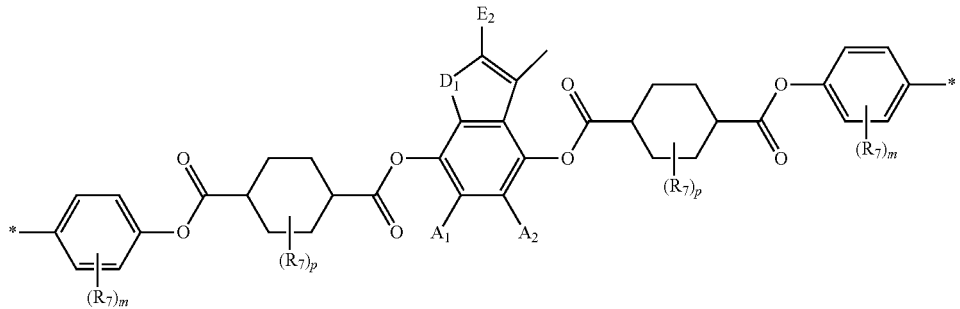

(1-7)

In Chemical Formula (1-6) and Chemical Formula (1-7), $L_1$, $A_1$, $A_2$, $D_1$, $D_2$, $E_1$ and $E_2$ are as defined in Chemical Formula (1-1) and Chemical Formula (1-2), each $R_7$ independently represents deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, a C2-C20 heterocycloalkyl group, a C6-C50 aryl group, or a C2-C50 heteroaryl group, each m is independently an integer of 0 to 4, and each p is independently an integer of 0 to 10.

Specific examples of the polymerizable compound according to an embodiment of the present disclosure may include compounds having the following structures.

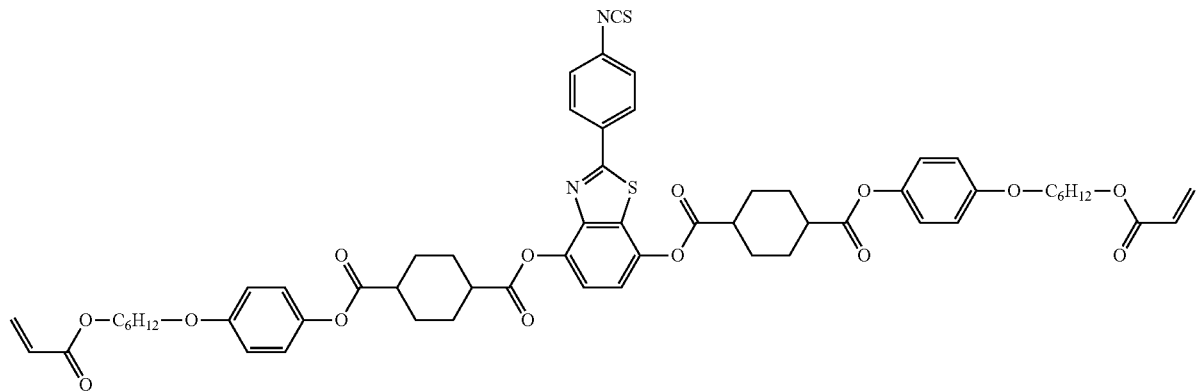
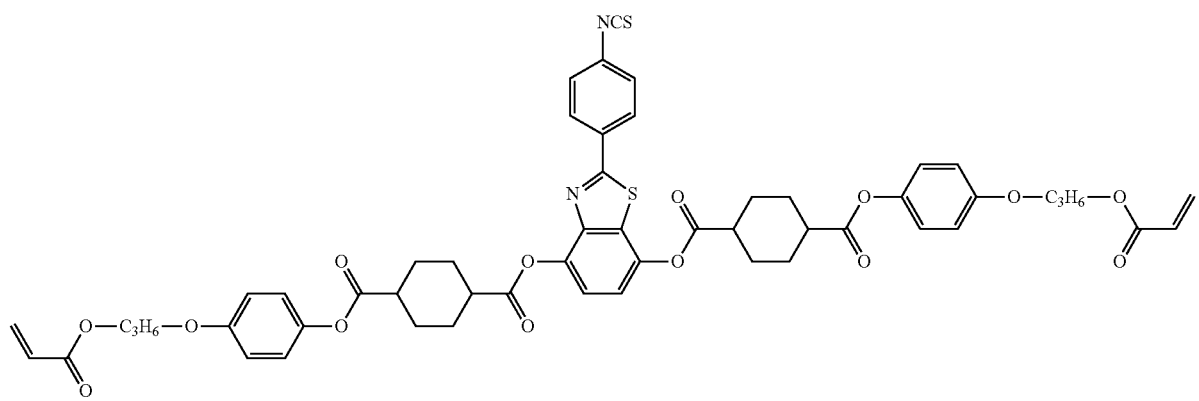
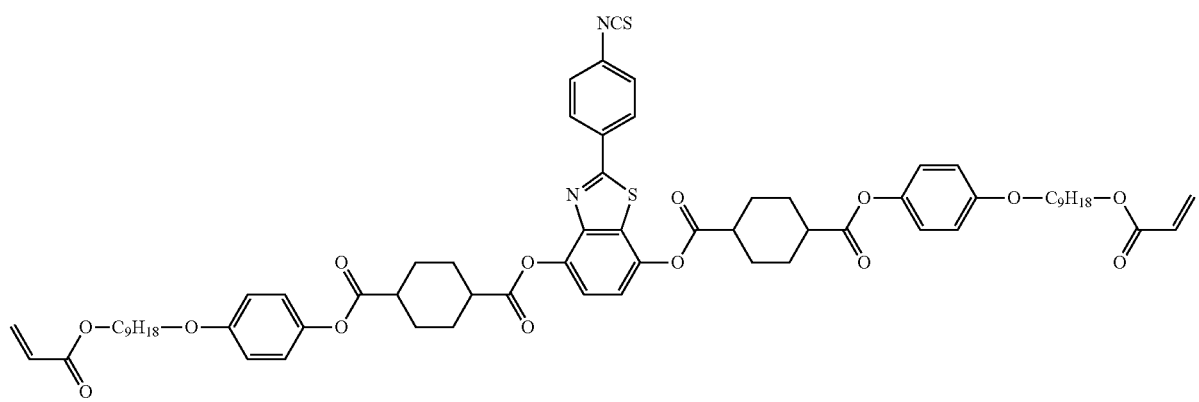
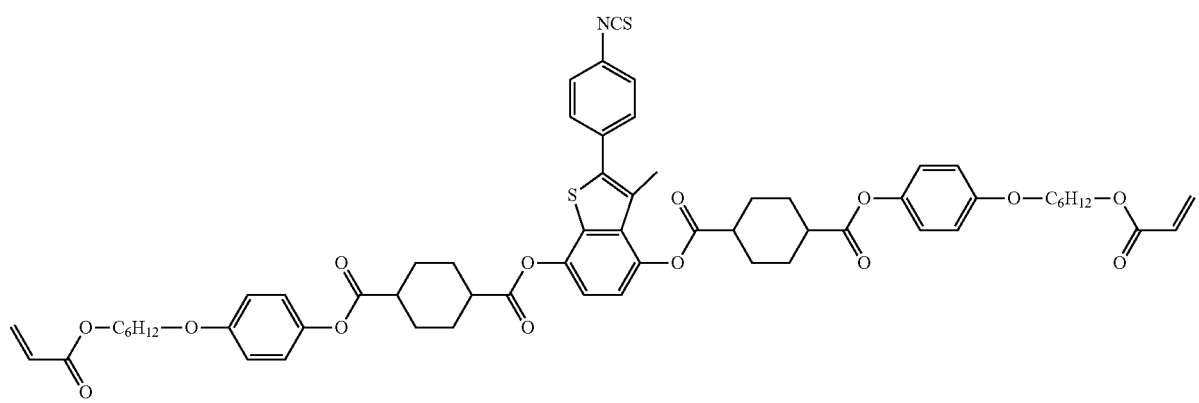

-continued

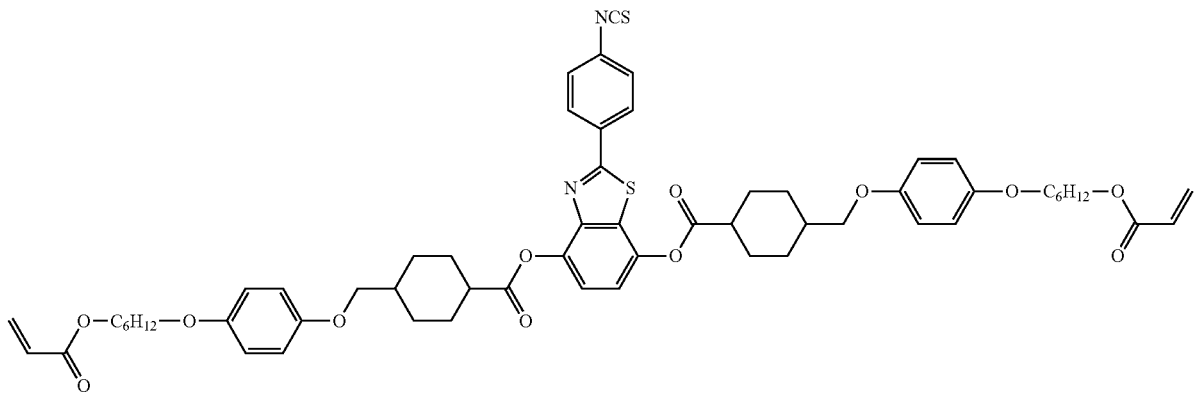

Another embodiment of the present disclosure pertains to a polymerizable composition including the polymerizable compound described above. The amount of the polymerizable compound may be about 0.5 parts by weight to about 50 parts by weight, for example about 1 part by weight to about 15 parts by weight, based on 100 parts by weight of the polymerizable composition.

The polymerizable composition may further include, in addition to the polymerizable compound described above, a polymerization initiator, another polymerizable compound, a non-polymerizable liquid crystal compound, a solvent, an additive, and the like. Here, the other polymerizable compound may be a polymerizable liquid crystal compound.

Also, specific examples of the other polymerizable compound are not limited, and may include the compounds represented by Chemical Formula (M1) and Chemical Formula (M2) below.

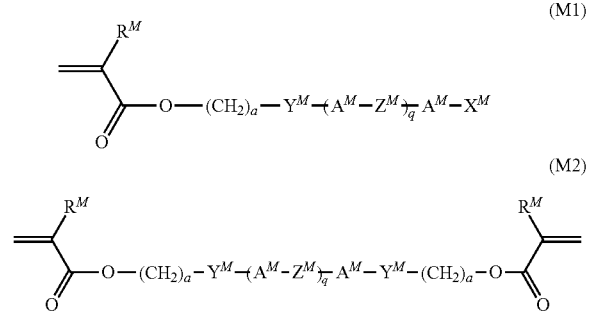

In Chemical Formula (M1) and Chemical Formula (M2), each $A^M$ is independently 1,4-phenylene, 1,4-cyclohexylene, 1,4 cyclohexenylene, pyridine-2,5-diyl, naphthalene-2,6-diyl or fluorene-2,7-diyl, in which at least one hydrogen may be substituted with fluorine, chlorine, cyano, hydroxy, formyl, trifluoroacetyl, difluoromethyl, trifluoromethyl, C1-C5 alkyl, C1-C5 alkoxy, C1-C5 alkyl ester or C1-C5 alkanoyl; each $Z^M$ is independently a single bond, —OCH$_2$—, —CH$_2$O—, —C(=O)O—, —OC(=O)—, —C(=O)S—, —SC(=O)—, —CC(=O)O—, —CONH—, —NHCO—, —CF$_2$O—, —OCF$_2$—, —CH$_2$CH$_2$—, —CF$_2$CF$_2$—, —CH=CHCOO—, —OCOCH=CH—, —CH$_2$CH$_2$COO—, —OCOCH$_2$CH$_2$—, —CH=CH—, —N=CH—, —CH=N—, —N=CCH$_3$—, —CCH$_3$=N—, —N=N— or —C≡C—; $X^M$ is hydrogen, fluorine, chlorine, trifluoromethyl, trifluoromethoxy, cyano, C1-C20 alkyl, C1-C20 alkenyl, C1-C20 alkoxy or C1-C20 alkyl ester; q is an integer of 1 to 4; a is an integer of 0 to 20; $R^M$ is hydrogen or methyl; and $Y^M$ is a single bond, —O—, —C(=O)O—, —OC(=O)— or —OC(=O)O—. Here, when q is 2 or more, $A^M$ and $Z^M$ may be different for each repeating unit.

A specific example of the non-polymerizable liquid crystal compound may be selected from among compounds listed in LiqCryst (LCI Publisher GmbH, Hamburg, Germany), which is a database of liquid crystal compounds. In addition, a known non-polymerizable liquid crystal compound may be used.

The polymerization initiator may include a photopolymerization initiator. Examples of the photopolymerization initiator may include benzoin compounds, benzophenone compounds, benzyl ketal compounds, a hydroxyketone compounds, α-amino ketone compounds, iodonium salts, sulfonium salts, and the like, specific examples of the photopolymerization initiator may include IRGACURE 907 (made by Chiba•Japan Co. Ltd.), IRGACURE 184 (made by Chiba•Japan Co. Ltd.), IRGACURE 651 (made by Chiba•Japan Co. Ltd.), IRGACURE 819 (made by Chiba•Japan Co. Ltd.), IRGACURE 250 (made by Chiba•Japan Co. Ltd.), IRGACURE 369 (made by Chiba•Japan Co. Ltd.), SEIKUOL BZ (made by Seiko Chemical Co. Ltd.), SEIKUOL Z (made by Seiko Chemical Co. Ltd.), SEIKUOL BEE (made by Seiko Chemical Co. Ltd.), KAYACURE BP100 (made by Nippon Kayaku Co. Ltd.), KAYACURE UVI-6992 (made by Dow Co. Ltd.), ADEKA OPTOMER SP-152 (made by ADEKA Corp.), ADEKA OPTOMER SP-170 (made by ADEKA Corp.), and the like.

The amount of the polymerization initiator may be about 0.1 parts by weight to about 30 parts by weight, particularly about 0.5 parts by weight to about 10 parts by weight, based on a total of 100 parts by weight of the polymerizable compound and other liquid crystal compounds. Given the above range, liquid crystal orientation may be superior and polymerization may be efficiently performed.

In order to facilitate application of the polymerizable composition of the present disclosure, the polymerizable composition may be diluted with a solvent, or individual components of the polymerizable composition may be added to a solvent to afford a polymerizable composition solution composed of the polymerizable composition and the solvent, and then the solution may be applied. Examples of the solvent may include ester-based solvents, amide-based solvents, alcohol-based solvents, ether-based solvents, glycol-monoalkyl-ether-based solvents, aromatic-hydrocarbon-based solvents, halogenated-aromatic-hydrocarbon-based solvents, aliphatic-hydrocarbon-based solvents, halogenated-aliphatic-hydrocarbon-based solvents, alicyclic-hydrocarbon-based solvents, ketone-based solvents, and acetate-based solvents.

Examples of the additive may include photosensitizers, chain transfer agents, antioxidants, ultraviolet absorbers, radical scavengers, light stabilizers, optically active compounds, silane-coupling agents, solvents, and other additives, within a range that does not impair the effects of the present disclosure.

Still another embodiment of the present disclosure pertains to an optical film including a polymer of the polymerizable compound.

The optical film may include a polymer obtained by applying a polymerizable composition containing the polymerizable compound on a substrate and then performing polymerization, so reverse-wavelength dispersibility thereof is vastly superior, as can be seen in the following examples.

Specifically, the optical film may have superior reverse-wavelength dispersibility when <Equation 1> and <Equation 2> below are satisfied at a thickness of about 0.1 μm to about 10 μm.

Re(450)/Re(550)≤0.970     <Equation 1>

1.020≤Re(650)/Re(550)     <Equation 2>

In Equations 1 and 2, Re(450) is the retardation value at a wavelength of 450 nm, Re(550) is the retardation value at a wavelength of 550 nm, and Re(650) is the retardation value at a wavelength of 650 nm.

Due to these characteristics, the optical film may be very suitable for use as a reverse-wavelength dispersion retardation film.

The substrate is not limited, and examples thereof may include glass, plastics, films, sheets, plates, etc., in which the materials or forms thereof are not limited, and the substrate may be a photoalignment layer, a polarizing layer, a protective layer, a retardation layer, etc., but is not limited thereto.

The optical film according to an embodiment of the present disclosure may be used as a reverse-wavelength dispersion retardation film, and may also be used as a broadband λ/4 plate or a λ/2 plate. In addition, it may be used as an optical film for a vertical alignment (VA) mode, and may be used for an anti-reflection (AR) film, a polarizing film, an elliptical polarizing film, a viewing angle enlargement film, or an optical compensation film for compensating the viewing angle of a transmissive liquid crystal display.

A better understanding of the polymerizable compound and the optical film according to embodiments of the present disclosure may be obtained through the following Preparation Examples and Examples. These Preparation Examples and Examples are merely set forth to illustrate the present disclosure and are not to be construed as limiting the scope of the present disclosure.

<Preparation Example 1-1> Synthesis of Compound 7

A compound 7 was synthesized starting from a compound 1 as shown in the following Scheme.

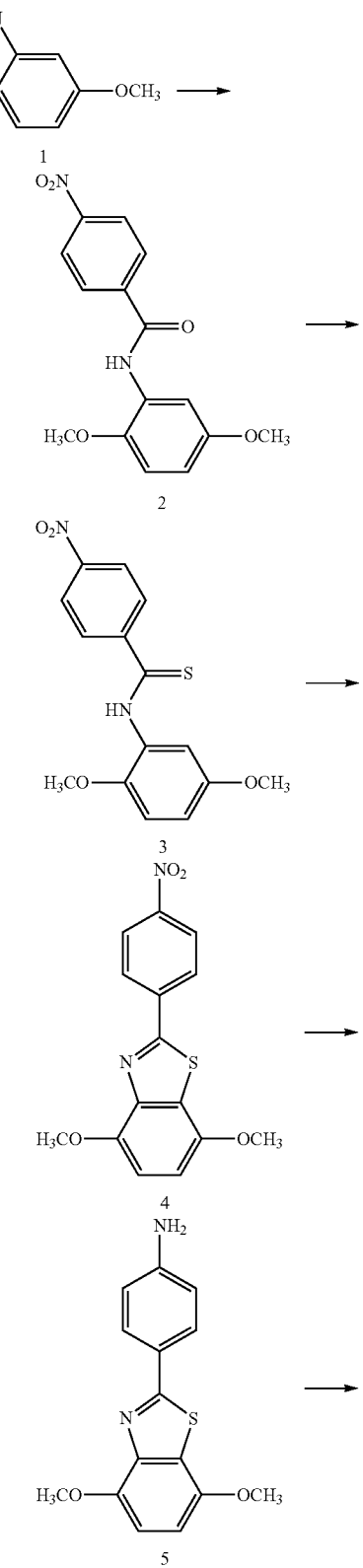

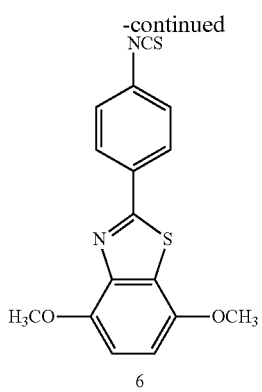

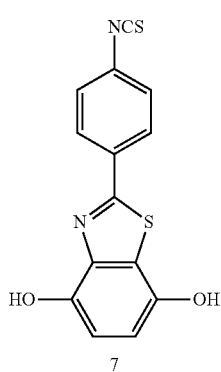

(1) A compound 1, 2,5-dimethoxyaniline (25 g, 0.163 mol), 36.34 g (0.195 mol) of 4-nitrobenzyl chloride, and 45.5 ml (0.326 mol) of triethylamine were dissolved in chloroform (700 ml) in a reaction vessel equipped with a stirrer, a thermometer, a cooling tube, and a temperature controller, followed by heating and reaction at 90° C. for 18 hr in a nitrogen atmosphere. After cooling to room temperature, the resulting reaction solution was diluted with water and dichloromethane, and the phases thereof were separated from each other. Thereafter, the organic layer was extracted and then dried over magnesium sulfate. The resulting solid was washed with hexane, thus obtaining a compound 2 (48.7 g). GC-MS (EI): m/z 302[M+H+]

(2) The compound 2 (48.7 g, 0.161 mol) and 42.8 g (0.105 mol) of a Lawesson reagent were dissolved in toluene (1 L) in a reaction vessel equipped with a stirrer, a thermometer, a cooling tube, and a temperature controller, and heated to reflux for 24 hr in a nitrogen atmosphere. The resulting reaction solution was cooled to room temperature and then concentrated. The concentrated residue was added with ethanol, after which the produced precipitate was filtered, thus obtaining a compound 3 (39.5 g). Yield 77%, GC-MS (EI): m/z 318[M+H+]

(3) The compound 3 (39.5 g, 0.124 mol), 54.45 g (0.165 mol) of potassium ferricyanide, and 10 ml of methanol were mixed with water (160 ml) in a reaction vessel equipped with a stirrer, a thermometer, a cooling tube, and a temperature controller. The resulting mixture was heated to 90° C., after which a 30% NaOH aqueous solution (132 ml) was added dropwise thereto over about 30 min, followed by heating and reaction at 90° C. for 2 hr. After cooling to room temperature, the precipitated solid was washed with water and hexane and filtered, thus obtaining a compound 4 (18.3 g). Yield 47%, GC-MS (EI): m/z 316[M+H+]

(4) The compound 4 (3.2 g, 0.010 mol) and 6.8 g (0.030 mol) of tin (II) chloride were dissolved in ethanol (60 ml) in a reaction vessel equipped with a stirrer, a thermometer, a cooling tube, and a temperature controller, and heated to reflux for 6 hr in a nitrogen atmosphere. After cooling to room temperature, the resulting reaction solution was diluted with 10% sodium hydroxide and dichloromethane, and the phases thereof were separated from each other. Thereafter, the organic layer was extracted and then dried over magnesium sulfate. The resulting solid was washed with methanol, thus obtaining a compound 5 (2.3 g). Yield 76%, GC-MS (EI): m/z 286[M+H+]

(5) The compound 5 (6.0 g, 0.021 mol) and 6.45 ml (0.046 mol) of triethylamine were dissolved in anhydrous THE (150 ml) in a reaction vessel equipped with a stirrer and a thermometer, followed by ice cooling to 0° C. To the reaction solution thus cooled, 3.2 ml (0.042 mol) of thiophosgene was added dropwise, after which the temperature was raised to room temperature and reaction was carried out for 2 hr. After termination of the reaction, the reaction mixture was filtered. The filtrate was concentrated and then eluted through a silica gel column using a solution of n-heptane and ethyl acetate at a volume ratio of 2:1, thus obtaining a compound 6 (2.2 g). Yield 33%, GC-MS (EI): m/z 328[M+H+]

(6) The compound 6 (1.1 g, 0.003 mol) was dissolved in chloroform (60 ml) in a reaction vessel equipped with a stirrer and a thermometer, followed by ice cooling to −60° C. in a nitrogen atmosphere. 10 ml of chloroform containing 2.3 ml (0.021 mol) of boron tribromide was then added dropwise thereto. Thereafter, the temperature was raised to room temperature and reaction was carried out for 12 hr. The resulting reaction solution was diluted with water and ethyl acetate, and the phases thereof were separated from each other. Thereafter, the organic layer was extracted, dried over magnesium sulfate, concentrated, and then eluted through a silica gel column using a THE solution, thereby obtaining a compound 7 (0.93 g). Yield 93%, GC-MS (EI): m/z 300 [M+H+]

<Preparation Example 1-2> Synthesis of Compound 10

A compound 10 was synthesized starting from a compound 8 as shown in the following Scheme.

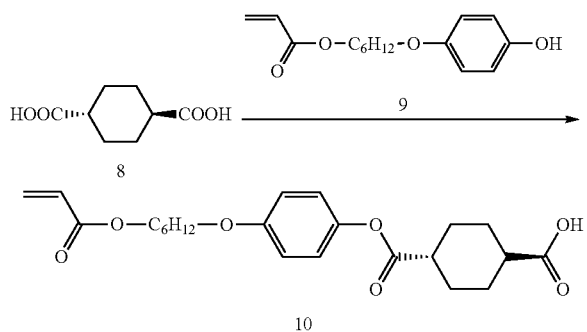

A compound 8, cyclohexyldicarboxylic acid (60.0 g, 0.348 mol), a compound 9 (18.4 g, 0.069 mol), 1.0 g (0.024 mol) of 3,5-dibutyl-4-hydroxytoluene, and 0.1 g (0.003 mol) of 4-dimethylaminopyridine were dissolved in N-methyl-2-pyrrolidone (120 ml) in a reaction vessel equipped with a stirrer, a thermometer, a cooling tube, and a temperature controller, the resulting reaction solution was heated to 45° C. in a nitrogen atmosphere, and 14.1 g (0.452 mol) of diisopropyl carbodiimide was added dropwise thereto over 1 hr, followed by reaction at 45° C. for 20 hr. After cooling to room temperature, 3.5 g (0.087 mol) of a sodium hydroxide aqueous solution (240 ml) was added dropwise thereto, and stirring was performed for 2 hr. The suspension thus obtained was washed with a solution of methanol and water at a volume ratio of 1:1, thereby obtaining a compound 10 (28.5 g) (Yield 97%).

$^1$H-NMR: δ (ppm) 1.44 to 1.62 (m, 8H), 1.72 (m, 2H), 1.80 (m, 2H), 2.16 (m, 2H), 2.22 (m, 2H), 2.41 (m, 1H), 2.53 (m, 1H), 3.94 (t, 2H), 4.18 (t, 2H), 5.82 (d, 1H), 6.13 (m, 1H), 6.40 (d, 1H), 6.88 (d, 2H), 6.97 (d, 2H).

<Preparation Example 1-3> Synthesis of Compound 11

A compound 11 was synthesized as shown in the following Scheme by reacting the compound 10 obtained in Preparation Example 1-2 with the compound 7 obtained in Preparation Example 1-1.

trated residue was added with a small amount of ethyl acetate and then with methanol (200 ml). The resulting precipitate was filtered, washed with methanol, and dried in a vacuum, thereby obtaining a compound 11 (2.5 g) (Yield 45%).

$^1$H-NMR: δ (ppm) 1.48 to 1.74 (m, 16H), 1.76 (m, 4H), 1.81 (m, 4H), 2.36 (m, 4H), 2.45 (m, 4H), 2.71 (m, 2H), 2.85 (m, 2H), 3.97 (t, 4H), 4.20 (t, 4H), 5.84 (d, 2H), 6.16 (m, 2H), 6.42 (d, 2H), 6.91 (d, 4H), 7.01 (d, 4H), 7.25 (s, 2H), 7.35 (d, 2H), 8.05 (d, 2H).

<Preparation Example 1-4> Synthesis of Compound 12

A compound 12 was synthesized in the same manner as in Preparation Example 1-2, with the exception that reaction was carried out as shown in the following Scheme using a compound 9-2 in lieu of the compound 9.

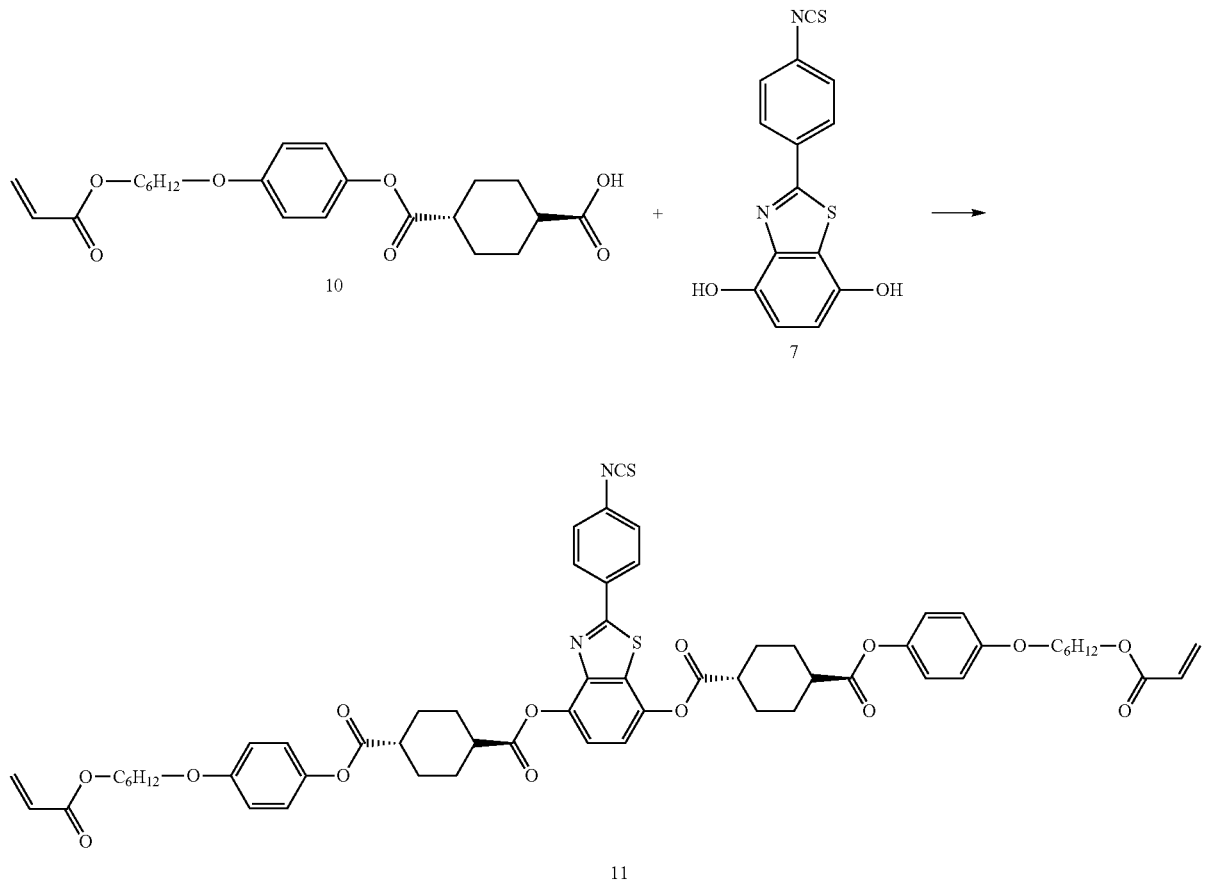

The compound 10 (4.18 g, 0.010 mol), the compound 7 (1.5 g, 0.005 mol), and 0.12 g (0.001 mol) of 4-dimethylaminopyridine were dissolved in THF (16 ml) in a reaction vessel equipped with a stirrer, a thermometer, a cooling tube, and a temperature controller, and then cooled to 0° C. in a nitrogen atmosphere, after which 2.47 g (0.012 mol) of dicyclohexyl carbodiimide was added dropwise thereto over 15 min. Thereafter, reaction was carried out at room temperature for 24 hr. After cooling to room temperature, the resulting reaction mixture was filtered. The filtrate was dried and then concentrated under reduced pressure. The concen-

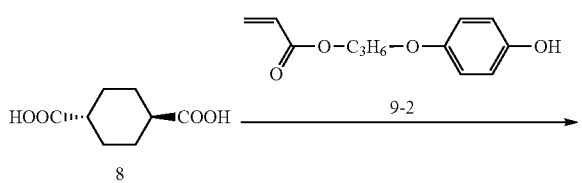

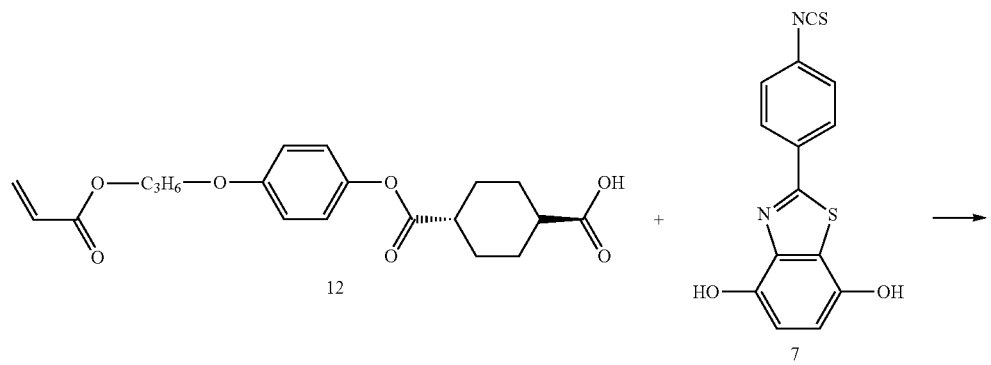

<Preparation Example 1-5> Synthesis of Compound 13

A compound 13 was synthesized in the same manner as in Preparation Example 1-3, with the exception that reaction was carried out as shown in the following Scheme using a compound 12 in lieu of the compound 10.

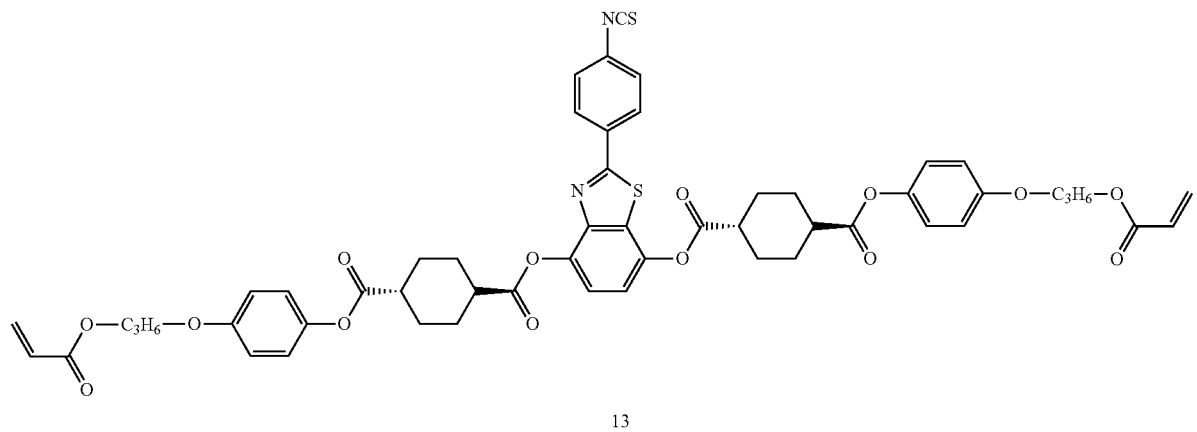

$^1$H-NMR: δ (ppm) 1.76 (m, 4H), 1.81 (m, 4H), 2.38 (m, 4H), 2.45 (m, 2H), 2.70 (m, 2H), 2.82 (m, 2H), 4.08 (t, 4H), 4.39 (t, 4H), 5.86 (d, 2H), 6.15 (m, 2H), 6.45 (d, 2H), 7.01 (d, 4H), 7.03 (d, 4H), 7.25 (s, 2H), 7.36 (d, 2H), 8.05 (d, 2H).

<Preparation Example 1-6> Synthesis of Compound 14

A compound 14 was synthesized in the same manner as in Preparation Example 1-2, with the exception that reaction was carried out as shown in the following Scheme using a compound 9-3 in lieu of the compound 9.

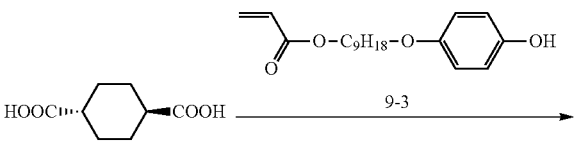
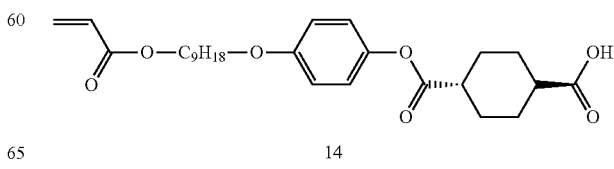

<Preparation Example 1-7> Synthesis of Compound 15

A compound 15 was synthesized in the same manner as in Preparation Example 1-3, with the exception that reaction was carried out as shown in the following Scheme using a compound 14 in lieu of the compound 10.

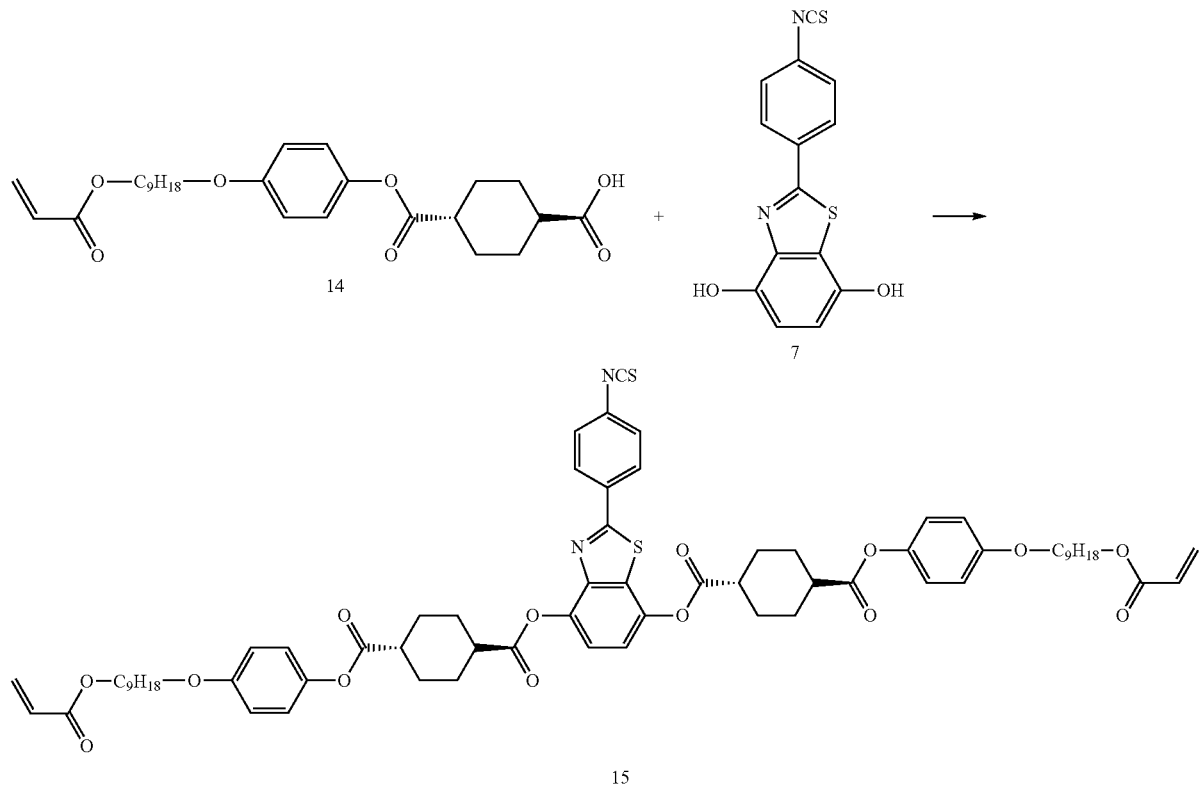

$^1$H-NMR: δ (ppm) 1.48 to 1.74 (m, 10H), 1.76 (m, 8H), 1.81 (m, 8H), 2.36 (m, 4H), 2.45 (m, 4H), 2.71 (m, 2H), 2.85 (m, 2H), 3.96 (t, 4H), 4.18 (t, 4H), 5.84 (d, 2H), 6.15 (m, 2H), 6.42 (d, 2H), 6.91 (d, 4H), 7.01 (d, 4H), 7.25 (s, 2H), 7.36 (d, 2H), 8.05 (d, 2H).

<Preparation Example 2-1> Synthesis of Compound 22

A compound 22 was synthesized starting from a compound 16 as shown in the following Scheme.

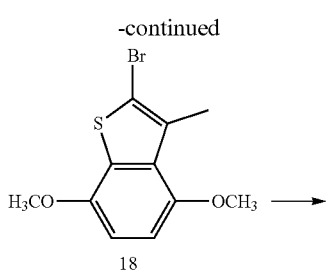

-continued

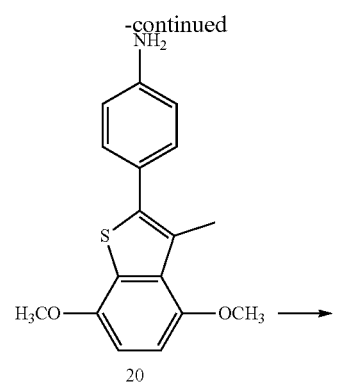

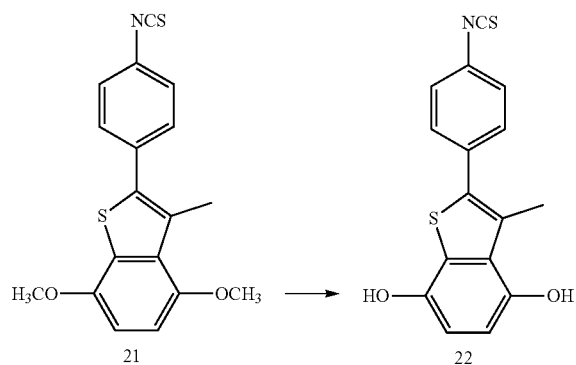

(1) A compound 16 (10.0 g, 0.058 mol), 16.3 g (0.176 mol) of chloroacetone, 10.7 g (0.087 mol) of NaCO$_3$/SiO$_2$, and 20.5 g (10 wt %) of PPA/SiO$_2$ were dissolved in 90 ml of chloroform in a reaction vessel equipped with a stirrer, a thermometer, a cooling tube, and a temperature controller, and heated to reflux for 6 hr in a nitrogen atmosphere. After cooling to room temperature, the resulting reaction mixture was washed with ethyl acetate and filtered. The filtrate was concentrated and then eluted through a silica gel column using a solution of n-heptane and ethyl acetate at a volume ratio of 2:1, thus obtaining a compound 17 (2.2 g). Yield 81%, GC-MS (EI): m/z 208[M+H+]

(2) The compound 17 (9.9 g, 0.047 mol) was dissolved in 60 ml of acetonitrile in a reaction vessel equipped with a stirrer, a thermometer, a cooling tube, and a temperature controller, followed by ice cooling to −60° C. in a nitrogen atmosphere. The reaction solution thus cooled was added with 8.9 g (0.049 mol) of N-bromosuccinimide. Thereafter, the temperature was raised to room temperature and reaction was carried out for 30 min. The reaction mixture was slowly added with 60 ml of distilled water and then stirred. The resulting solid was filtered and washed with 20 ml of distilled water and acetonitrile at a volume ratio of 1:1, thus obtaining a compound 18 (12.4 g). Yield 98%, GC-MS (EI): m/z 249[M+H+]

(3) The compound 18 (8.7 g, 0.034 mol), 9.5 g (0.033 mol) of 4,4,5,5-tetramethyl-2-(4-nitrophenyl)-1,3,2-dioxaborolane, and 1.9 g (0.001 mol) of tetrakis(triphenylphosphine)palladium(0) were dissolved in 195 ml of dioxane in a reaction vessel equipped with a stirrer, a thermometer, a cooling tube, and a temperature controller, added with 65 ml of a 2 M NaCO$_3$ aqueous solution, and then heated to reflux for 6 hr. After cooling to room temperature, the resulting reaction solution was diluted with a saturated aluminum chloride aqueous solution and dichloromethane, and the phases thereof were separated from each other. Thereafter, the organic layer was extracted and then dried over magnesium sulfate. The concentrated residue was eluted through a silica gel column using a solution of n-heptane and ethyl acetate at a volume ratio of 2:1, thus obtaining compound 19 (9.9 g). Yield 91%, GC-MS (EI): m/z 329[M+H+]

(4) The compound 19 (9.9 g, 0.030 mol) and 20.5 g (0.090 mol) of tin chloride were dissolved in 200 ml of ethanol in a reaction vessel equipped with a stirrer, a thermometer, a cooling tube, and a temperature controller, and heated to reflux for 2 hr in a nitrogen atmosphere. After cooling to room temperature, the resulting reaction solution was diluted with a 2 N potassium hydroxide aqueous solution and ethyl acetate, and the phases thereof were separated from each other. Thereafter, the organic layer was extracted and then dried over magnesium sulfate. The concentrated residue was eluted through a silica gel column using a solution of dichloromethane and THF at a volume ratio of 10:1, thus obtaining a compound 20 (9.9 g). Yield 74%, GC-MS (EI): m/z 299[M+H+]

(5) The compound 20 (6.8 g, 0.030 mol) and 7.0 ml (0.069 mol) of triethylamine were dissolved in anhydrous THF (100 ml) in a reaction vessel equipped with a stirrer, a thermometer, a cooling tube, and a temperature controller, followed by ice cooling to 0° C. To the reaction solution thus cooled, 3.5 ml (0.045 mol) of thiophosgene was added dropwise. Thereafter, the temperature was raised to room temperature and reaction was carried out for 2 hr. After termination of the reaction, the reaction mixture was filtered. The filtrate was concentrated and then eluted through a silica gel column using a chloromethane solution, thus obtaining a compound 21 (4.5 g). Yield 58%, GC-MS (EI): m/z 341[M+H+]

(6) The compound 21 (4.5 g, 0.013 mol) was dissolved in chloroform (250 ml) in a reaction vessel equipped with a thermometer, followed by ice cooling to −60° C. in a nitrogen atmosphere. To the reaction solution thus cooled, 20 ml of chloroform containing 8.9 ml (0.035 mol) of boron tribromide was added dropwise, after which the temperature was raised to room temperature and reaction was carried out for 12 hr. The resulting reaction solution was diluted with water and ethyl acetate, and the phases thereof were separated from each other. Thereafter, the organic layer was extracted, dried over magnesium sulfate, concentrated, and then eluted through a silica gel column using a THF solution, thereby obtaining a compound 22 (3.7 g). Yield 90%, GC-MS (EI): m/z 313[M+H+].

<Preparation Example 2-2> Synthesis of Compound 23

A compound 23 was synthesized as shown in the following Scheme by reacting the compound 10 obtained in Preparation Example 1-2 with the compound 22 obtained in Preparation Example 2-1.

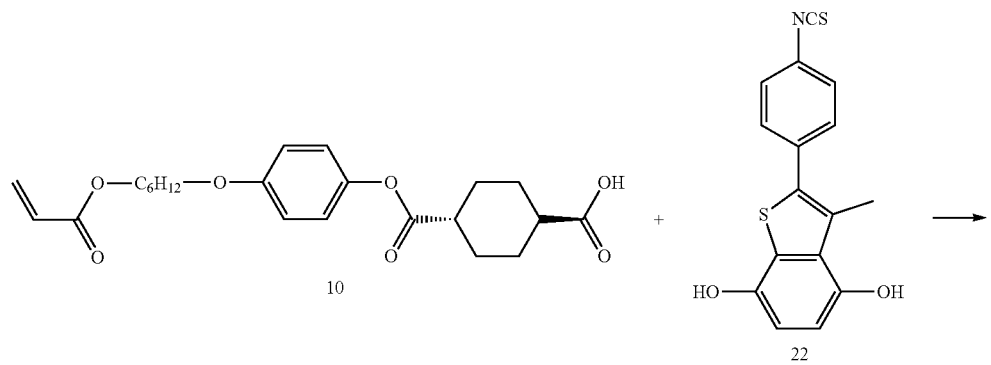

10

22

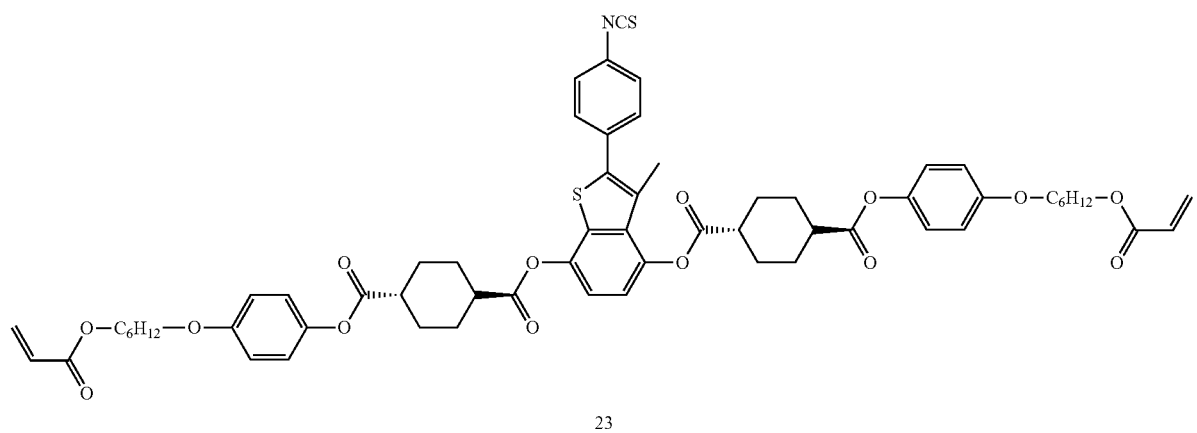

23

The compound 10 (9.9 g, 0.024 mol), the compound 22 (3.7 g, 0.012 mol), and 0.28 g (0.002 mol) of 4-dimethyl-aminopyridine were dissolved in THF (200 ml) in a reaction vessel equipped with a stirrer, a thermometer, a cooling tube, and a temperature controller, the reaction solution was cooled to 0° C. in a nitrogen atmosphere, and 5.85 g (0.028 mol) of dicyclohexyl carbodiimide was added dropwise thereto over 15 min, followed by reaction at room temperature for 24 hr. After cooling to room temperature, the resulting reaction mixture was filtered. The filtrate was dried, and then concentrated under reduced pressure. The concentrated residue was added with a small amount of ethyl acetate and then with methanol (200 ml). The resulting precipitate was filtered, washed with methanol, and dried in a vacuum, thereby obtaining a compound 23 (5.26 g) (Yield 40%).

$^1$H-NMR: δ (ppm) 1.48 to 1.74 (m, 16H), 1.76 (m, 4H), 1.81 (m, 4H), 2.32 (S, 3H), 2.38 (m, 8H), 2.46 (m, 2H), 2.65 (m, 2H), 3.97 (t, 4H), 4.20 (t, 4H), 5.84 (d, 2H), 6.17 (m, 2H), 6.42 (d, 2H), 6.89 (d, 4H), 6.99 (d, 4H), 7.18 (m, 2H), 7.27 (d, 2H), 7.38 (d, 2H).

<Preparation Example 3-1> Synthesis of Compound 25

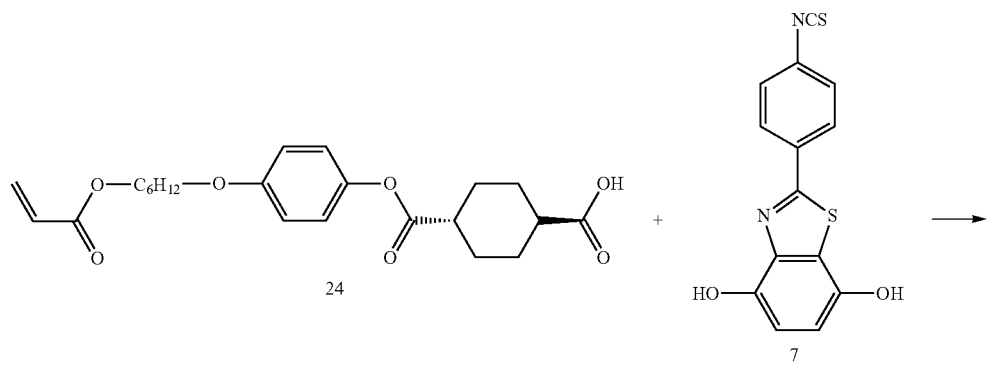

24

7

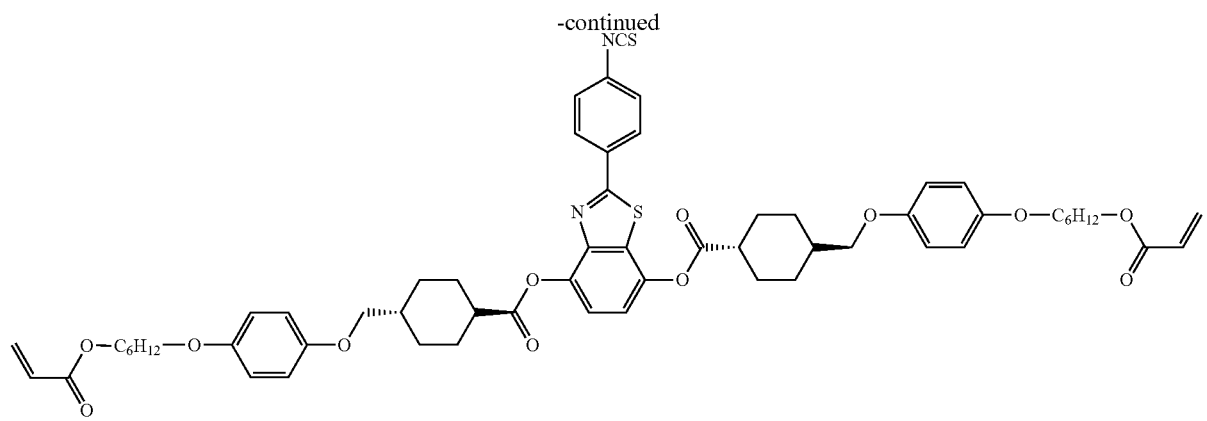

25

The compound 7 (1.1 g, 0.003 mol), the compound 24 (3.1 g, 0.007 mol), and 0.1 g (0.0006 mol) of 4-dimethylaminopyridine were dissolved in dichloromethane (50 ml) in a reaction vessel equipped with a stirrer, a thermometer, a cooling tube, and a temperature controller, the reaction solution was cooled to 0° C. in a nitrogen atmosphere, and 1.12 g (0.008 mol) of diisopropyl carbodiimide was added dropwise thereto over 10 min, followed by reaction at room temperature for 24 hr. After cooling to room temperature, the resulting reaction mixture was filtered. The filtrate was dried and then concentrated under reduced pressure. The concentrated residue was added with a small amount of ethyl acetate and then with methanol (200 ml). The resulting precipitate was filtered, washed with methanol, and dried in a vacuum, thereby obtaining a compound 25 (1.60 g) (Yield 40%).

$^1$H-NMR: δ (ppm) 1.48 to 1.74 (m, 16H), 1.76 (m, 4H), 1.81 (m, 4H), 2.30 (m, 4H), 2.39 (m, 4H), 2.68 (m, 2H), 2.77 (m, 2H), 3.80 (t, 4H), 3.94 (t, 4H), 4.19 (t, 4H), 5.84 (d, 2H), 6.14 (m, 2H), 6.42 (d, 2H), 6.84 (d, 4H), 6.88 (d, 4H), 7.23 (s, 2H), 7.35 (d, 2H), 8.05 (d, 2H).

Examples and Comparative Example> Manufacture of Optical Film

A 2% aqueous solution of polyvinyl alcohol (Mw 31000-50000, Aldrich) was applied on a glass substrate, heated, and dried, thus obtaining a film having a thickness of 100 nm. The surface of the film thus obtained was subjected to rubbing treatment, after which the surface subjected to rubbing treatment was slit-coated with the solution of each of Examples 1 to 5 and Comparative Example 1, having the compositions shown in Table 1 below. Thereafter, drying for 3 min on a hot plate and then irradiation with UV light at 1200 mJ/cm$^2$ were performed, thereby obtaining each optical film having the thickness shown in Table 2 below.

In Table 1 below, "%" represents the amount (weight) based on the total weight of the solution. "Irg 819" represents the photoinitiator, IRGACURE 819, and "BYK-361N" represents a leveling agent responsible for leveling the surface.

In addition, LC242 in Comparative Example 1 is a compound having the following structure.

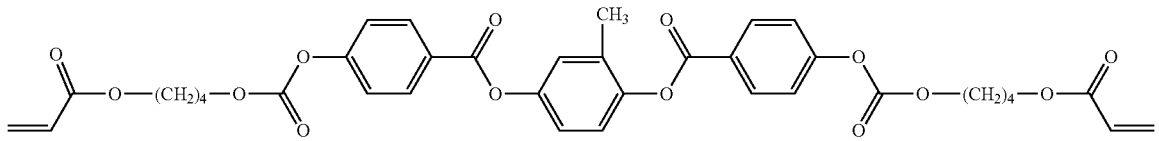

TABLE 1

| | Compound 11 (%) | Compound 13 (%) | Compound 15 (%) | Compound 23 (%) | Compound 25 (%) | LC242 (%) | Photopolymerization initiator Irg 819 (%) | Leveling agent BYK-361N (%) | Solvent |
|---|---|---|---|---|---|---|---|---|---|
| Example 1 | 10 | 0 | 0 | 0 | 0 | 0 | 0.5 | 0.01 | Anisole |
| Example 2 | 0 | 10 | 0 | 0 | 0 | 0 | 0.5 | 0.01 | Anisole |
| Example 3 | 0 | 0 | 10 | 0 | 0 | 0 | 0.5 | 0.01 | Anisole |
| Example 4 | 0 | 0 | 0 | 10 | 0 | 0 | 0.5 | 0.01 | Anisole |
| Example 5 | 0 | 0 | 0 | 0 | 10 | 0 | 0.5 | 0.01 | Anisole |
| Comparative Example 1 | 0 | 0 | 0 | 0 | 0 | 10 | 0.5 | 0.01 | Anisole |

<Test Example 1> Measurement of Optical Properties

Figure 2:
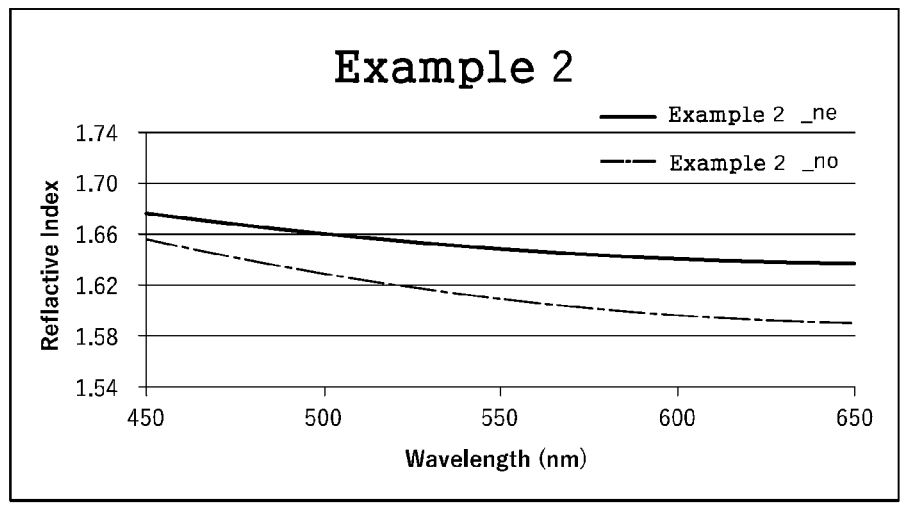
Figure 3:
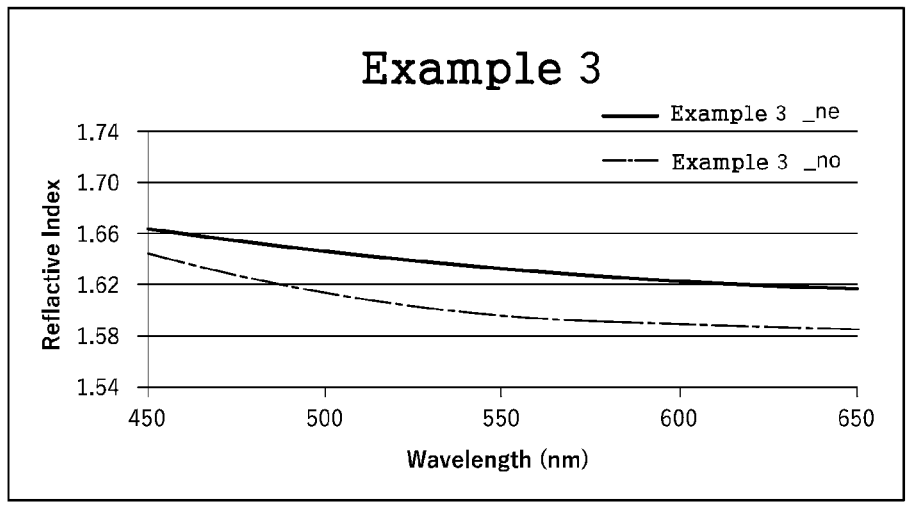
Figure 4:
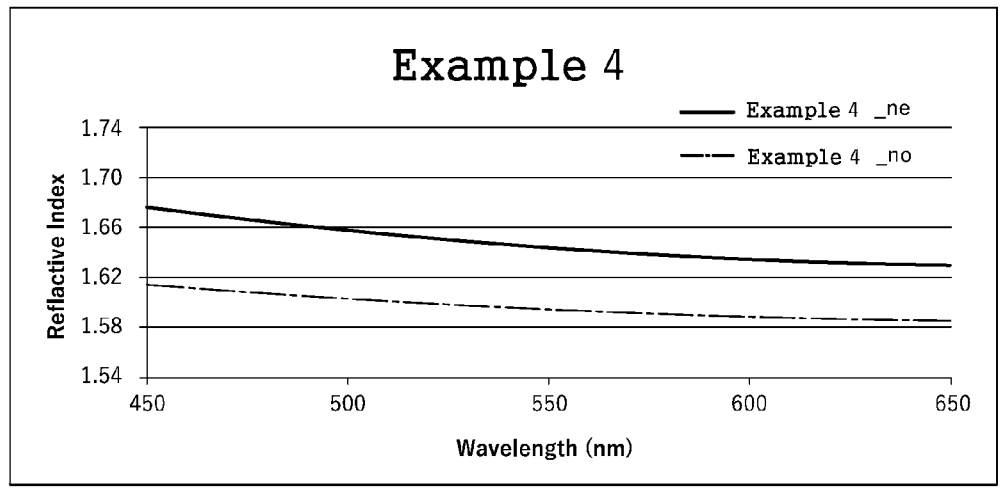
Figure 5:
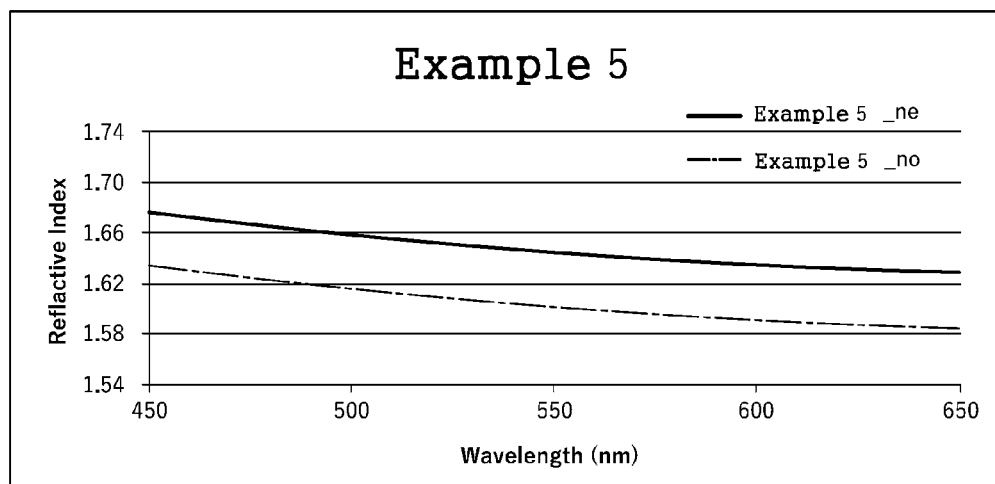

In the wavelength range of 380 nm to 780 nm, the refractive index and retardation value of each of the manufactured optical films were measured using a measurement device (RETS-100, Otsuka Co. Ltd.), and the retardation value Re(450) at a wavelength of 450 nm, the retardation value Re(550) at a wavelength of 550 nm, and the retardation value Re(650) at a wavelength of 650 nm were determined. The results of the ordinary (no) and extraordinary (ne) refractive indexes of the optical films according to Examples 1 to 5 are shown in FIGS. 1 to 5, the results of the retardation values at a wavelength of 550 nm and the retardation ratios of the optical films according to Examples 1 to 5 and Comparative Example 1 are shown in Table 2 below.

TABLE 2

|  | Re(550) (nm) | Re(450)/ Re(550) | Re(650)/ Re(550) | Optical film thickness d (μm) |
| --- | --- | --- | --- | --- |
| Example 1 | 67.8 | 0.937 | 1.037 | 2.5 |
| Example 2 | 142.7 | 0.955 | 1.026 | 3.4 |
| Example 3 | 51.1 | 0.950 | 1.029 | 2.1 |
| Example 4 | 71.1 | 0.970 | 1.021 | 2.1 |
| Example 5 | 74.8 | 0.964 | 1.021 | 2.0 |
| Comparative Example 1 | 141.0 | 1.075 | 0.978 | 1.1 |

As shown in Table 2 and in the drawings, the polymerizable compound according to an embodiment of the present disclosure was used alone or in combination with other known polymerizable liquid crystal compounds and other components to afford a composition, and uniform orientation appeared in any form, thereby reducing wavelength dependence on the refractive index anisotropy of the material or exhibiting superior reverse-wavelength dispersibility.

In contrast, Comparative Example 1 showed positive-wavelength dispersion characteristics. Specifically, the reverse-wavelength dispersion material is characterized in that the value of Re(450/550) is less than 1 and the value of Re(650/550) is greater than 1 in the retardation ratio, but in Comparative Example 1, the value of Re(450/550) is 1.075 and the value of Re(650/550) is 0.978. As is apparent from the results of Table 2, the polymerizable compound of the present disclosure exhibited reverse-wavelength dispersion characteristics, unlike Comparative Example 1.

While this disclosure has been described in connection with what is presently considered to be practical example embodiments, it is to be understood that the inventive concepts are not limited to the disclosed example embodiments. On the contrary, the inventive concepts are intended to cover various modifications and equivalent arrangements included within the spirit and scope of the appended claims.

What is claimed is:

1. A compound of Chemical Formula (1-6) below, wherein polymerizable groups are introduced both ends of the compound:

Chemical Formula (1-6)

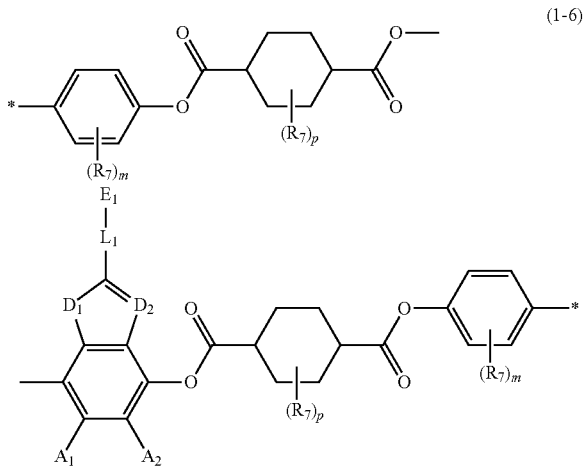

(1-6)

wherein, in Chemical Formula (1-6),
$A_1$ and $A_2$ each independently represent hydrogen, deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, or a C6-C50 aryl group,
$D_1$ represents —S—,
$D_2$ represents =N—,
$L_1$ is a direct bond or a C2-C10 alkynylene group having a triple bond, and
each $R_7$ independently represents deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, or a C6-C50 aryl group, and
each m is independently an integer of 0 to 4,
each p is independently an integer of 0 to 10,
wherein $E_1$ is represented by any one selected from the group consisting of Chemical Formulas Y-1, Y-5, Y-10 to Y-13 below:

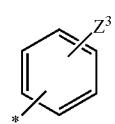

Y-1

-continued

Y-5
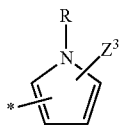

Y-10
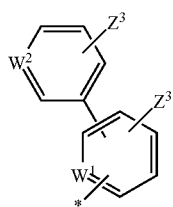

Y-11
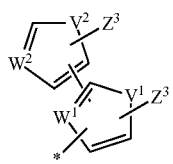

Y-12
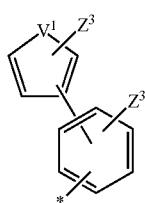

Y-13
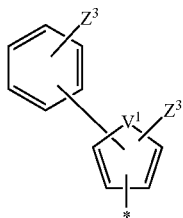

wherein, in Chemical Formulas Y-1, Y-5, Y-10 to Y-13, $Z_3$ of Chemical Formula Y-1 represents an isothiocyanate group or a thiocyanate group, $Z^3$ and R of Chemical Formula Y-2, Y5 and Y10 to Y13 each independently represent deuterium, a halogen, an amino group, a cyano group, a nitro group, a nitroso group, a sulfamoyl group, an isothiocyanate group, a thiocyanate group, a carboxyl group, a C1-C30 alkyl group, a C1-C30 alkylsulfinyl group, a C1-C30 alkylsulfonyl group, a C1-C30 alkylsulfanyl group, a C1-C12 fluoroalkyl group, a C2-C30 alkenyl group, a C1-C30 alkoxy group, a C1-C12 N-alkylamino group, a C2-C20 N,N-dialkylamino group, a C1-C6 N-alkylsulfamoyl group, a C2-C12 N,N-dialkylsulfamoyl group, a C3-C20 cycloalkyl group, or a C6-C50 aryl group, in which, $V^1$ and $V^2$ each independently represent —S— or —O—, $W^1$ to $W^5$ each independently represent —$CR_4$= or —N=, in which $R_4$ independently represents hydrogen or a C1-C4 alkyl group.

2. The compound of claim 1, wherein

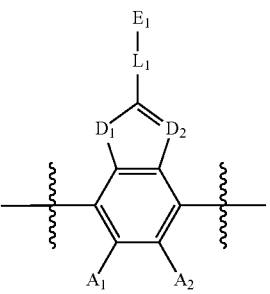

of Chemical Formula (1-6) has a structure represented by any one selected from the group consisting of the following chemical formulas:

(1-1-1)
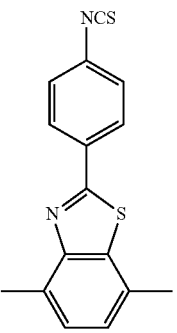

(1-1-2)
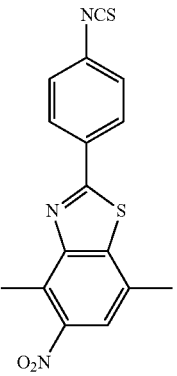

(1-1-3)
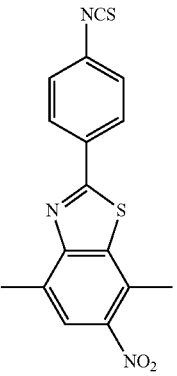

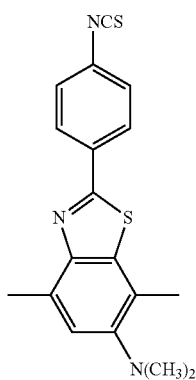 (1-1-4)
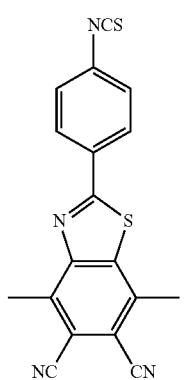 (1-1-8)
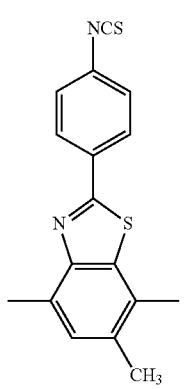 (1-1-5)
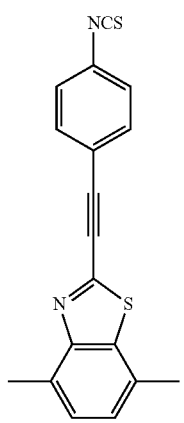 (1-1-9)
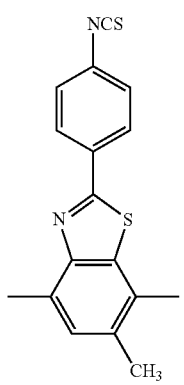 (1-1-6)
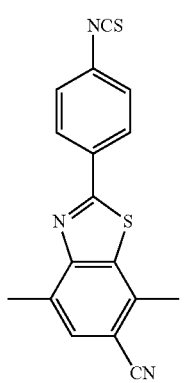 (1-1-7)
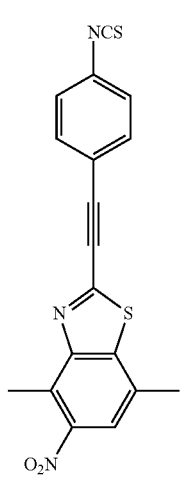 (1-1-10)

(1-1-11)
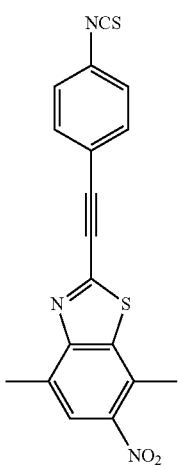
(1-1-14)
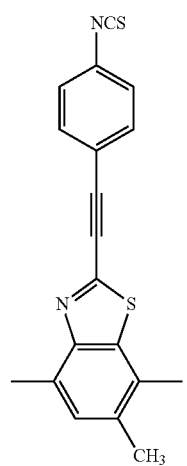
(1-1-12)
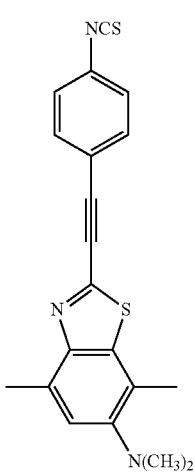
(1-1-15)
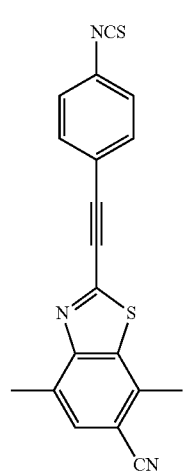
(1-1-13)
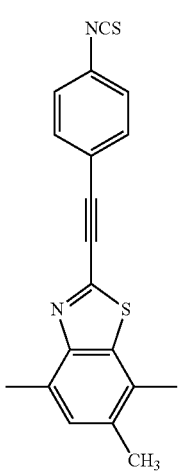
(1-1-16)
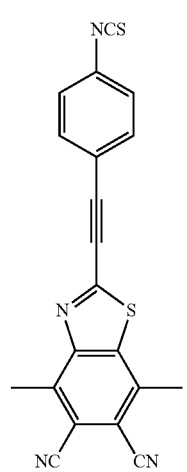

3. The compound of claim 1, which is represented by any one selected from among the following chemical formulas:
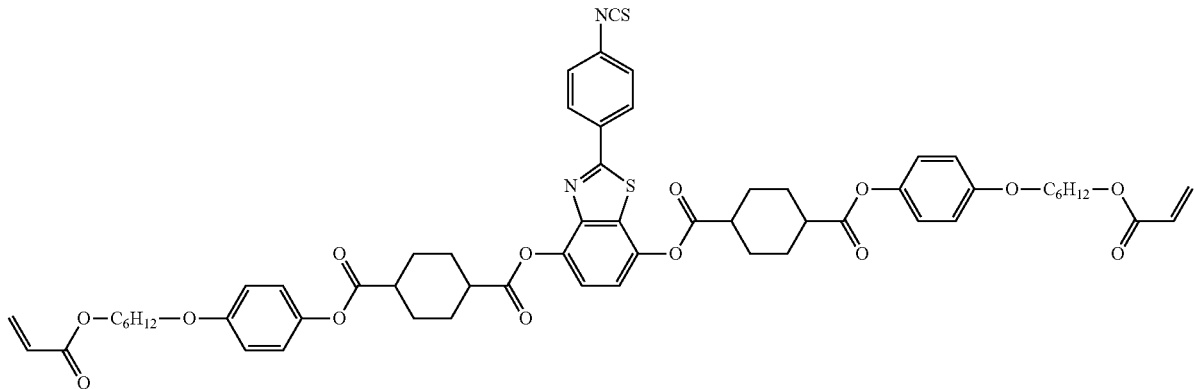
11
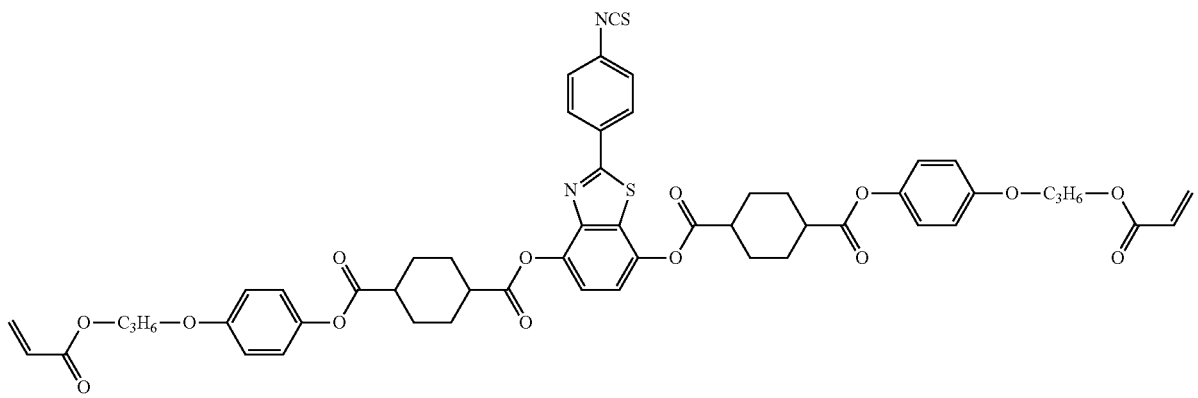
13
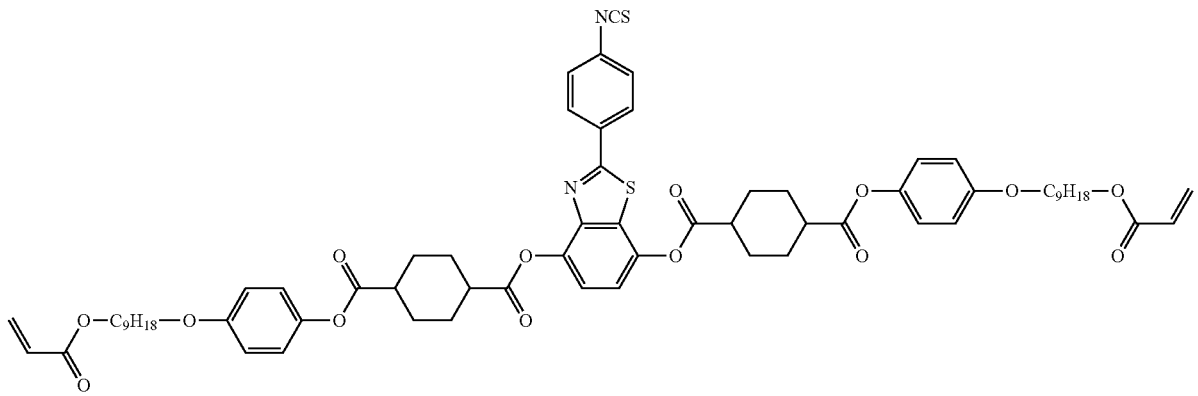
15

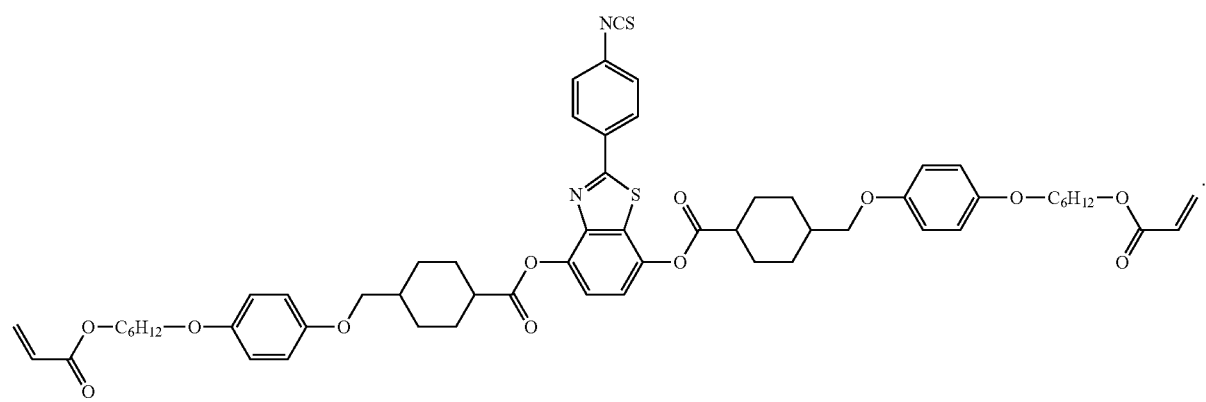
* * * * *